(12) United States Patent
Engelthaler et al.

(10) Patent No.: US 9,994,917 B2
(45) Date of Patent: Jun. 12, 2018

(54) **METHODS TO DETECT AND GENOTYPE *CRYTOCOCCUS* SPECIES**

(71) Applicants: THE TRANSLATION GENOMICS RESEARCH INSTITUTE, Phoenix, AZ (US); ARIZONA BOARD OF REGENTS ON BEHALF OF NORTHERN ARIZONA UNIVERSITY, Flagstaff, AZ (US)

(72) Inventors: David Engelthaler, Flagstaff, AZ (US); Elizabeth Driebe, Flagstaff, AZ (US); Erin Kelley, Flagstaff, AZ (US); Paul Keim, Flagstaff, AZ (US)

(73) Assignees: The Translational Genomics Research Institute, Phoenix, AZ (US); Arizona Board of Regents on Behalf of Northern Arizona University, Flagstaff, AZ (US)

( * ) Notice: Subject to any disclaimer, the term of this patent is extended or adjusted under 35 U.S.C. 154(b) by 54 days.

(21) Appl. No.: 14/819,529

(22) Filed: Aug. 6, 2015

(65) Prior Publication Data
US 2016/0040217 A1   Feb. 11, 2016

Related U.S. Application Data

(60) Provisional application No. 62/033,769, filed on Aug. 6, 2014.

(51) Int. Cl.
C12Q 1/68 (2018.01)
C07H 21/02 (2006.01)
C07H 21/04 (2006.01)

(52) U.S. Cl.
CPC ....... *C12Q 1/689* (2013.01); *C12Q 2600/156* (2013.01); *C12Q 2600/158* (2013.01); *C12Q 2600/16* (2013.01)

(58) Field of Classification Search
None
See application file for complete search history.

(56) References Cited

PUBLICATIONS

Kelley et al BMC Microbiology. Published online May 13, 2014. 14:125, pp. 1-15.*
Meyer et al. Med Mycol. 2009. 47(6): 561-570, pp. 1-14.*
Kidd et al. PNAS. Dec. 2004. 101: 17258-17263.*

* cited by examiner

*Primary Examiner* — Carla J Myers

(57) ABSTRACT

Embodiments of the invention provide a method of genotyping a *C. gattii* sample, which can include forming a plurality of mixtures for nucleic amplification. The method can include amplification of specific sequences within the *C. gattii* genome that can provide definitive genotype information to distinguish between one or more types or subtypes of *C. gattii*.

17 Claims, 1 Drawing Sheet

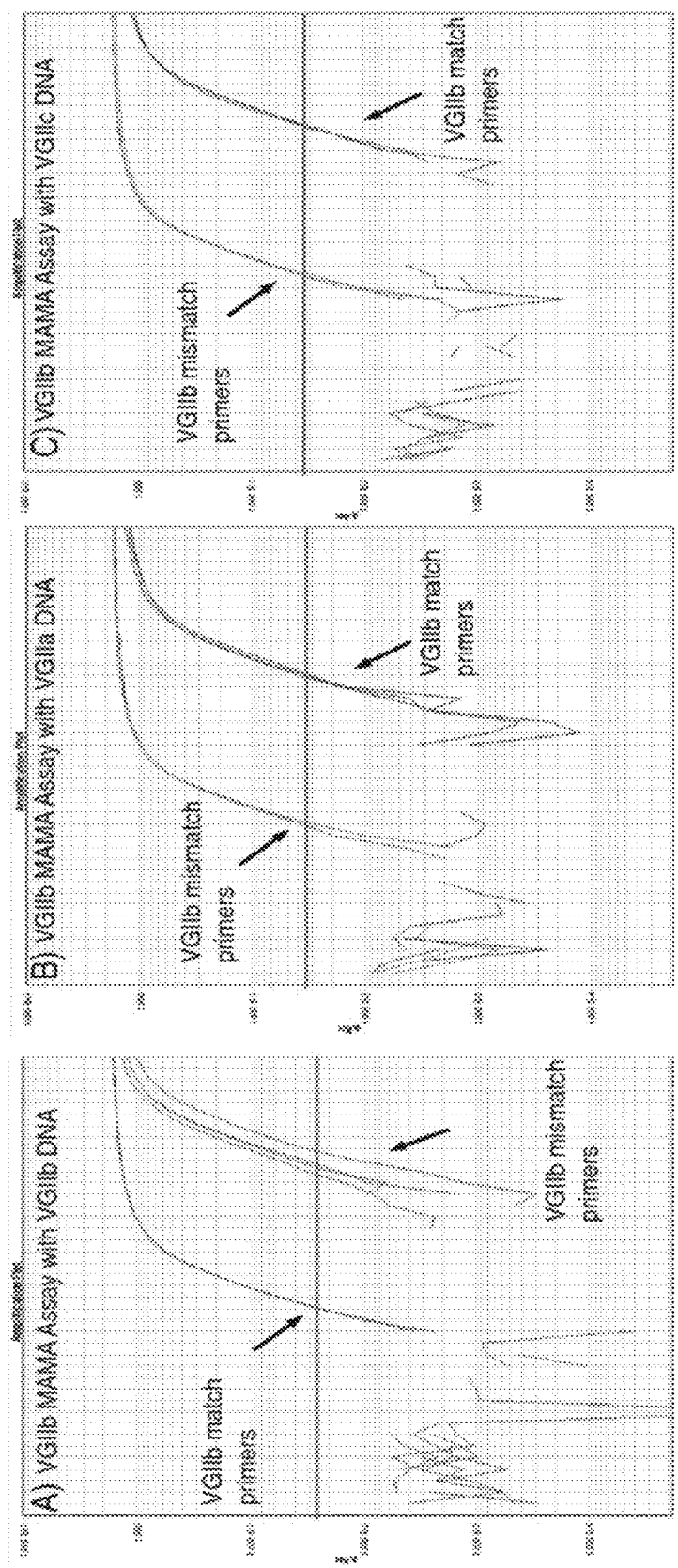

SEQUENCE LISTING

<160> NUMBER OF SEQ ID NOS: 27

<210> SEQ ID NO 1
<211> LENGTH: 24
<212> TYPE: DNA
<213> ORGANISM: Artificial Sequence
<220> FEATURE:
<223> OTHER INFORMATION: Primer

<400> SEQUENCE: 1
agactgtccc aatgtcaagc tttc                                              24

<210> SEQ ID NO 2
<211> LENGTH: 24
<212> TYPE: DNA
<213> ORGANISM: Artificial Sequence
<220> FEATURE:
<223> OTHER INFORMATION: Primer

<400> SEQUENCE: 2
gccttgtatg tggtaacacc agtg                                              24

<210> SEQ ID NO 3
<211> LENGTH: 26
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (2)..(2)
<223> OTHER INFORMATION: w is an "a" or a "t"

<400> SEQUENCE: 3
gwgccttgta tgtggtaaca ccagta                                            26

<210> SEQ ID NO 4
<211> LENGTH: 24
<212> TYPE: DNA
<213> ORGANISM: Artificial Sequence
<220> FEATURE:
<223> OTHER INFORMATION: Primer

<400> SEQUENCE: 4
agactgtccc aatgtcaagc tttc                                          24

<210> SEQ ID NO 5
<211> LENGTH: 28
<212> TYPE: DNA
<213> ORGANISM: Artificial Sequence
<220> FEATURE:
<223> OTHER INFORMATION: Primer

<400> SEQUENCE: 5
attaacctta gtgttggaga ccttgact                                      28

<210> SEQ ID NO 6
<211> LENGTH: 25
<212> TYPE: DNA
<213> ORGANISM: Artificial Sequence
<220> FEATURE:
<223> OTHER INFORMATION: Primer

<400> SEQUENCE: 6
aaccttagtg ttggagacct tgaca                                         25

<210> SEQ ID NO 7
<211> LENGTH: 20
<212> TYPE: DNA
<213> ORGANISM: Artificial Sequence
<220> FEATURE:
<223> OTHER INFORMATION: Primer

<400> SEQUENCE: 7
cccagcaacc ttgatctgga                                               20

<210> SEQ ID NO 8
<211> LENGTH: 25
<212> TYPE: DNA
<213> ORGANISM: Artificial Sequence
<220> FEATURE:
<223> OTHER INFORMATION: Primer

<400> SEQUENCE: 8
agctgctcta agagacacat catca                                         25

<210> SEQ ID NO 9
<211> LENGTH: 25
<212> TYPE: DNA
<213> ORGANISM: Artificial Sequence
<220> FEATURE:
<223> OTHER INFORMATION: Primer

<400> SEQUENCE: 9
agctgctcta agagacacat catcc                                         25

<210> SEQ ID NO 10
<211> LENGTH: 22
<212> TYPE: DNA
<213> ORGANISM: Artificial Sequence
<220> FEATURE:
<223> OTHER INFORMATION: Primer

<400> SEQUENCE: 10
aatcgctcgt cctcatatga ca                                            22

```
<210> SEQ ID NO 11
<211> LENGTH: 20
<212> TYPE: DNA
<213> ORGANISM: Artificial Sequence
<220> FEATURE:
<223> OTHER INFORMATION: Primer

<400> SEQUENCE: 11
gtaggcggtg ggataaggtg                                             20

<210> SEQ ID NO 12
<211> LENGTH: 21
<212> TYPE: DNA
<213> ORGANISM: Artificial Sequence
<220> FEATURE:
<223> OTHER INFORMATION: Primer

<400> SEQUENCE: 12
ggtaggcggt gggataaggt a                                           21

<210> SEQ ID NO 13
<211> LENGTH: 25
<212> TYPE: DNA
<213> ORGANISM: Artificial Sequence
<220> FEATURE:
<223> OTHER INFORMATION: Primer

<400> SEQUENCE: 13
cgttaatttg gttgtttgac aacct                                       25

<210> SEQ ID NO 14
<211> LENGTH: 22
<212> TYPE: DNA
<213> ORGANISM: Artificial Sequence
<220> FEATURE:
<223> OTHER INFORMATION: Primer

<400> SEQUENCE: 14
agcaactcac gcagaaacag ac                                          22

<210> SEQ ID NO 15
<211> LENGTH: 23
<212> TYPE: DNA
<213> ORGANISM: Artificial Sequence
<220> FEATURE:
<223> OTHER INFORMATION: Primer

<400> SEQUENCE: 15
gagcaactca cgcagaaaca gat                                         23

<210> SEQ ID NO 16
<211> LENGTH: 22
<212> TYPE: DNA
<213> ORGANISM: Artificial Sequence
<220> FEATURE:
<223> OTHER INFORMATION: Primer

<400> SEQUENCE: 16
tgacattggg acagtctgca at                                          22

<210> SEQ ID NO 17
<211> LENGTH: 20
<212> TYPE: DNA
<213> ORGANISM: Artificial Sequence
<220> FEATURE:
<223> OTHER INFORMATION: Primer
```

<400> SEQUENCE: 17
actgctgctt ctcccgttgt                                            20

<210> SEQ ID NO 18
<211> LENGTH: 19
<212> TYPE: DNA
<213> ORGANISM: Artificial Sequence
<220> FEATURE:
<223> OTHER INFORMATION: Primer

<400> SEQUENCE: 18
ctgctgcttc tcccgttga                                             19

<210> SEQ ID NO 19
<211> LENGTH: 26
<212> TYPE: DNA
<213> ORGANISM: Artificial Sequence
<220> FEATURE:
<223> OTHER INFORMATION: Primer

<400> SEQUENCE: 19
acccagtcat taaccttagt gttgga                                     26

<210> SEQ ID NO 20
<211> LENGTH: 22
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (13)..(13)
<223> OTHER INFORMATION: y is a "c" or a "t"

<400> SEQUENCE: 20
ctcgttcgtc aaycacgtta ga                                         22

<210> SEQ ID NO 21
<211> LENGTH: 21
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (12)..(12)
<223> OTHER INFORMATION: y is a "c" or a "t"

<400> SEQUENCE: 21
tcgttcgtca aycacgttag c                                          21

<210> SEQ ID NO 22
<211> LENGTH: 26
<212> TYPE: DNA
<213> ORGANISM: Artificial Sequence
<220> FEATURE:
<223> OTHER INFORMATION: Primer

<400> SEQUENCE: 22
gagccttgta tgtggtaaca ccagta                                     26

<210> SEQ ID NO 23
<211> LENGTH: 26
<212> TYPE: DNA
<213> ORGANISM: Artificial Sequence
<220> FEATURE:
<223> OTHER INFORMATION: Primer

```
<400> SEQUENCE: 23
gtgccttgta tgtggtaaca ccagta                                          26

<210> SEQ ID NO 24
<211> LENGTH: 22
<212> TYPE: DNA
<213> ORGANISM: Artificial Sequence
<220> FEATURE:
<223> OTHER INFORMATION: Primer

<400> SEQUENCE: 24
ctcgttcgtc aaccacgtta ga                                              22

<210> SEQ ID NO 25
<211> LENGTH: 22
<212> TYPE: DNA
<213> ORGANISM: Artificial Sequence
<220> FEATURE:
<223> OTHER INFORMATION: Primer

<400> SEQUENCE: 25
ctcgttcgtc aatcacgtta ga                                              22

<210> SEQ ID NO 26
<211> LENGTH: 21
<212> TYPE: DNA
<213> ORGANISM: Artificial Sequence
<220> FEATURE:
<223> OTHER INFORMATION: Primer

<400> SEQUENCE: 26
tcgttcgtca accacgttag c                                               21

<210> SEQ ID NO 27
<211> LENGTH: 21
<212> TYPE: DNA
<213> ORGANISM: Artificial Sequence
<220> FEATURE:
<223> OTHER INFORMATION: Primer

<400> SEQUENCE: 27
tcgttcgtca atcacgttag c                                               21
```

METHODS TO DETECT AND GENOTYPE *CRYTOCOCCUS* SPECIES

CROSS REFERENCE TO RELATED APPLICATIONS

This application claims the priority of U.S. provisional application with application No. 62/033,769 filed Aug. 6, 2014, the contents of each of which are hereby incorporated by reference in their entirety for all purposes.

STATEMENT REGARDING FEDERALLY SPONSORED RESEARCH

This invention was made with government support under AI098059 awarded by the National Institutes of Health. The government has certain rights in the invention.

INCORPORATION-BY-REFERENCE OF MATERIAL ELECTRONICALLY FILED

Incorporated by reference in its entirety herein is a computer-readable nucleotide/amino acid sequence listing submitted concurrently herewith and identified as follows: One 6 kilobyte ASCII (text) file named "Crypto_ST25" created Jul. 30, 2015.

FIELD OF INVENTION

The present invention is generally related to methods of identifying pathogenic fungi and specifically related to methods and kits of detecting and/or genotyping *Cryptococcus* species.

BACKGROUND OF THE INVENTION

Cryptococcosis, a potentially fatal fungal disease, has primarily been observed in immune-compromised individuals and mainly associated with *Cryptococcus neoformans* infection. It is now recognized that *Cryptococcus gattii*, once considered to be a variety of the *Cryptococcus neoformans* complex, is also capable of causing serious disease in immunocompetent individuals and animals [1,2]. *C. gattii* has been associated with a number of tree species in tropical and subtropical regions [3]. More recently, *C. gattii* caused an outbreak that began in 1999 on Vancouver Island, British Columbia and has spread to mainland Canada and the US Pacific Northwest [4]. This outbreak is unique in that it marked the identification of a *Cryptococcus* species in a new climatic region (from tropical to temperate), habitat (from tropical trees to temperate; e.g., Douglas Fir) and host disease (from primary neurologic to primary pulmonary) [3,5].

Recent epidemiological studies of *C. gattii* in North America provide insight into the organism's geographical expansion as well as the distribution of molecular genotypes [6-9]. *C. gattii* has been classically classified into four molecular types by MLST/AFLP, VGI/AFLP4, VGII/AFLP6, VGIII/AFLP5, VGIV/AFLP7 [3,5], with additional molecular types recently identified [10]. Interestingly, molecular types have been associated with significant differences in disease type [3,5], antifungal susceptibilities [3,5,10], and severity and outcome [3,5].

Contemporary methods for genotyping *C. gattii* are PCR-restriction fragment length polymorphism (PCR-RFLP), amplified fragment length polymorphism (AFLP), multilocus microsatellite typing (MLMT), multilocus sequence typing (MLST), and most recent, matrix-assisted laser desorption ionization-time-of-flight mass spectrometry (MALDI-TOF MS) [11-14]. High resolution melting (HRM) is a method that has been used to identify the *Cryptococcus neoformans-Cryptococcus gattii* complex, though it has not been employed for genotyping within either species [15]. PCR-RFLP and AFLP require extensive lab work involving restriction enzyme digestion and gel electrophoresis [11]. Results are based on interpretation of gel electrophoresis profiles and as such, are not readily transferred or analyzed between laboratories. MLST, which requires DNA sequencing of seven housekeeping genes, is the preferred genotyping method for *C. gattii* and is easily transferable between laboratories [16]. MLMT allows for finer genotype resolution than MLST and has high reproducibility between laboratories [14]. In some laboratories, real-time PCR is a preferable option to methods involving DNA sequencing (MLMT and MLST), which require either out-sourcing to a sequencing capable laboratory or investment in, and the maintenance of, an in-house instrument. Although MALDI-TOF MS shows promise as a new genotyping method, instrumentation is expensive and thus prohibitive for many public health laboratories. Conversely, real-time PCR instruments are becoming ubiquitous, easily maintained, and the use of unlabeled primers and no probe makes reagents inexpensive [17]. Therefore, real-time PCR is an accessible and increasing popular technology for widespread molecular epidemiological efforts.

Given these concerns and motivations, there is a demonstrated need in the art for a panel of real-time PCR assays, based on mismatch amplification mutation assay (MAMA) methodology, for rapid and sensitive molecular detection and/or genotyping of *Cryptococcus gattii* molecular types (VGI-VGIV) and the dominant North American VGII subtypes (VGIIa-c) [18,19]. MAMA, a form of allele-specific PCR (ASPCR), employs primers that are designed for SNP genotyping.

SUMMARY

Some embodiments of the invention provide methods of genotyping a *C. gattii* sample. For example, the methods may include adding a first oligonucleotide to a first mixture comprising the sample, wherein the first oligonucleotide added to the first mixture includes a sequence selected from the group consisting of SEQ ID NO. 7, SEQ ID NO. 8, and SEQ ID NO. 9 and adding a first oligonucleotide to a second mixture comprising the sample, wherein the first oligonucleotide added to the second mixture includes a sequence selected from the group consisting of SEQ ID NO. 13, SEQ ID NO. 14, and SEQ ID NO. 15. The method may also include subjecting the first and second mixtures to conditions that allow nucleic acid amplification and determining the genotype of the *Cryptococcus gattii* sample on the basis of results of the nucleic acid amplifications of the first and second mixtures.

Other embodiments may further provide additional methods for genotyping a *C. gattii* sample. The methods may include adding a first oligonucleotide to a first mixture comprising the sample, wherein the first oligonucleotide added to the first mixture includes a sequence selected from the group consisting of SEQ ID NO. 4, SEQ ID NO. 5, and SEQ ID NO. 6. The methods can also include creating at least one more mixture using the following methods: (i) adding a first oligonucleotide to a mixture comprising the sample, wherein the first oligonucleotide added to the second mixture includes a sequence selected from the group consisting of SEQ ID NO. 1, SEQ ID NO. 2, and SEQ ID NO. 3; (ii) adding a first oligonucleotide to a mixture comprising the sample, wherein the first oligonucleotide added to the second mixture includes a sequence selected from the group consisting of SEQ ID NO. 16, SEQ ID NO. 17, and SEQ ID NO. 18; or (iii) adding a first oligonucleotide to a mixture comprising the sample, wherein the first oligonucleotide added to the second mixture includes a sequence selected from the group consisting of SEQ ID NO. 19, SEQ ID NO. 20, and SEQ ID NO. 21. The method may also include subjecting the mixtures to conditions that allow nucleic acid amplification and determining the genotype of the *Cryptococcus gattii* sample on the basis of results of the nucleic acid amplifications of the mixtures.

Further methods of genotyping a *C. gattii* sample provided by some embodiments of the invention include adding a first oligonucleotide to a first mixture comprising the sample, wherein the first oligonucleotide added to the first mixture includes a sequence selected from the group consisting of SEQ ID NO. 1, SEQ ID NO. 2, and SEQ ID NO. 3 and adding a first oligonucleotide to a second mixture comprising the sample, wherein the first oligonucleotide added to the second mixture includes a sequence selected from the group consisting of SEQ ID NO. 4, SEQ ID NO. 5, and SEQ ID NO. 6. The method also includes subjecting the first and second mixtures to conditions that allow nucleic acid amplification and determining the genotype of the *Cryptococcus gattii* sample on the basis of results of the nucleic acid amplifications of the first and second mixtures.

Additional objectives, advantages and novel features will be set forth in the description which follows or will become apparent to those skilled in the art upon examination of the drawings and detailed description which follows.

BRIEF DESCRIPTION OF THE DRAWINGS

FIG. 1 is a series of PCR amplification plots that illustrate a VGII subtype genotyping assay. (A) The VGIIb match primers amplify VGIIb DNA efficiently and yield a lower Ct value than the VGIIb mismatch primers, resulting in a VGIIb genotype call. (B) The VGIIb mismatch primers amplify VGIIa DNA more efficiently than the VGIIb match primers, resulting in a non-VGIIb genotype call. (C) VGIIb mismatch primers amplify VGIIc DNA more efficiently than the VGIIb match primers, again resulting in a non-VGIIb genotype call.

DETAILED DESCRIPTION

In the following description, and for the purposes of explanation, numerous specific details are set forth in order to provide a thorough understanding of the various aspects of the invention. It will be understood, however, by those skilled in the relevant arts, that the present invention may be practiced without these specific details. In other instances, known structures and devices are shown or discussed more generally in order to avoid obscuring the invention.

Aspects and applications of the invention presented here are described below in the drawings and detailed description of the invention. Unless specifically noted, it is intended that the words and phrases in the specification and the claims be given their plain, ordinary, and accustomed meaning to those of ordinary skill in the applicable arts. Inventors are fully aware that they can be their own lexicographers if desired.

Herein disclosed are methods and kits that can be employed to detect, genotype, and/or quantify one or more species of *Cryptococcus* (e.g., *Cryptococcus gatii*). For example, some of the methods disclosed herein can be used to determine whether an unidentified *C. gatii* sample should be classified as one of the four classic genotypes, VGI/AFLP4, VGII/AFLP, VGIII/AFLP5, VGIV/AFLP7 (referred to as VGI-VGIV herein). Moreover, in some aspects, the methods disclosed herein can be used to further elucidate if an unidentified *C. gatii* sample is one of the North American VGII subtypes (i.e., VGIIa, VGIIb, or VGIIc). In order to make diagnostic or genotyping determinations, some aspects of the methods disclosed herein may rely on the assessment/determination of a status of one or more markers.

A marker may be any molecular structure produced by a cell, expressed inside the cell, accessible on the cell surface, or secreted by the cell. A marker may be any protein, carbohydrate, fat, nucleic acid, catalytic site, or any combination of these such as an enzyme, glycoprotein, cell membrane, virus, cell, organ, organelle, or any uni- or multimolecular structure or any other such structure now known or yet to be disclosed whether alone or in combination. A marker may also be called a target and the terms are used interchangeably.

A marker may be represented by the sequence of a nucleic acid from which it can be derived. Examples of such nucleic acids include miRNA, tRNA, siRNA, mRNA, cDNA, or genomic DNA sequences. While a marker may be represented by the sequence of a single nucleic acid strand (e.g. 5'→3'), nucleic acid reagents that bind the marker may also bind to the complementary strand (e.g. 3'→5'). Alternatively, a marker may be represented by a protein sequence. The concept of a marker is not limited to the products of the exact nucleic acid sequence or protein sequence by which it may be represented. Rather, a marker encompasses all molecules that may be detected by a method of assessing the expression of the marker.

When a nucleic acid includes a particular sequence, the sequence may be a part of a longer nucleic acid or may be the entirety of the sequence. The nucleic acid may contain nucleotides 5' of the sequence, 3' of the sequence, or both. The concept of a nucleic acid including a particular sequence further encompasses nucleic acids that contain less than the full sequence that are still capable of specifically detecting a marker. Nucleic acid sequences may be identified by the IUAPC letter code which is as follows: A—Adenine base; C—Cytosine base; G—guanine base; T or U—thymine or uracil base. M-A or C; R-A or G; W-A or T; S-C or G; Y-C or T; K-G or T; V-A or C or G; H-A or C or T; D-A or G or T; B-C or G or T; N or X-A or C or G or T. Note that T or U may be used interchangeably depending on whether the nucleic acid is DNA or RNA. A reagent capable of binding to a nucleic acid sequence having less than 60% 70%, 80%, 90%, 95%, 99% or 100% identity to the identifying sequence may still be encompassed by the invention if it is still capable of binding to its complimentary sequence and/or facilitating nucleic acid amplification of a desired sequence. Although a nucleic acid sequence represented by the sequence of a single nucleic acid strand (e.g. the 5'3' strand) the totality of reagents that bind to the sequence also includes all reagents capable of binding to the complementary strand (e.g the 3'→5' strand). If a sequence is represented in degenerate form; for example through the use of codes other than A, C, G, T, or U; the concept of a nucleic acid including the sequence also encompasses a mixture of nucleic acids of different sequences that still meet the conditions imposed by the degenerate sequence. Examples of molecules encompassed by a marker represented by a particular sequence or structure include point mutations, single nucleotide polymorphisms (SNPs), silent mutations, deletions, frameshift mutations, translocations, alternative splicing derivatives, differentially methylated sequences, truncations, soluble forms of cell membrane associated markers, and any other variation that results in a product that may be identified as the marker. The following nonlimiting examples are included for the purposes of clarifying this concept: If expression of a specific marker in a sample is assessed by PCR, and if the sample expresses an DNA sequence different from the sequence used to identify the specific marker by one or more nucleotides, but the marker may still be detected using PCR, then the specific marker encompasses the sequence present in the sample. A marker may also be represented by a protein sequence, which includes mutated and differentially modified protein sequences.

The invention may comprise methods of detecting and/or genotyping unidentified C. gatii in a sample. A sample may be derived from anywhere that fungus or any part of a fungal body may be found including soil, air, water, solid surfaces (whether natural or artificial) culture media, foodstuffs, and any interfaces between or combinations of these elements. Additionally, a sample may be derived from a subject, such as a plant or animal, including humans. Samples derived from animals include but are not limited to biopsy or other in vivo or ex vivo analysis of prostate, breast, skin, muscle, facia, brain, endometrium, lung, head and neck, pancreas, small intestine, blood, liver, testes, ovaries, colon, skin, stomach, esophagus, spleen, lymph node, bone marrow, kidney, placenta, or fetus. Samples derived from subjects may also take the form of a fluid sample such as peripheral blood, lymph fluid, ascites, serous fluid, pleural effusion, sputum, bronchial wash, bronchioalveolar lavage fluid (BALF), cerebrospinal fluid, semen, amniotic fluid, lacrimal fluid, stool, urine, hair, or any other source in which a fungus, or any part of a fungus might be present. Samples collected from a plant may be collected from part of a plant or from an entire plant. Samples may be collected by any method now known or yet to be disclosed, including swiping or swabbing an area or orifice, removal of a piece of tissue as in a biopsy, or any method known to collect bodily fluids. Samples may also include *C. gatii* that has been previously isolated from one or more prior samples and grown in an isolated environment (e.g., a laboratory). Thereafter, one or more biomolecules (e.g., nucleic acids or protein) can be isolated from the *C. gatii* for used in the methods disclosed herein.

Direct methods of detecting the presence of a marker include but are not limited to any form of DNA sequencing including Sanger, next generation sequencing, pyrosequencing, SOLID sequencing, massively parallel sequencing, pooled, and barcoded DNA sequencing or any other sequencing method now known or yet to be disclosed; PCR-based methods such as real-time PCR, quantitative PCR, or any combination of these; allele specific ligation; comparative genomic hybridization; array based genotyping including SNP genotyping, or any other method that allows the detection of a particular nucleic acid sequence within a sample or enables the differentiation of one nucleic acid from another nucleic acid that differs from the first nucleic acid by one or more nucleotides. A sample may be suspected of including a nucleic acid from a fungus of interest. A subject may be any organism that may be infected by a virus including bacteria, plants, animals, chordates, mammals, humans, insects, endangered species, or any other organism of agricultural, environmental, or other significance.

In Sanger Sequencing, a single-stranded DNA template, a primer, a DNA polymerase, nucleotides and a label such as a radioactive label conjugated with the nucleotide base or a fluorescent label conjugated to the primer, and one chain terminator base comprising a dideoxynucleotide (ddATP, ddGTP, ddCTP, or ddTTP, are added to each of four reaction (one reaction for each of the chain terminator bases). The sequence may be determined by electrophoresis of the resulting strands. In dye terminator sequencing, each of the chain termination bases is labeled with a fluorescent label of a different wavelength which allows the sequencing to be performed in a single reaction.

In pyrosequencing, the addition of a base to a single stranded template to be sequenced by a polymerase results in the release of a pyrophosphate upon nucleotide incorporation. An ATP sulfurylase enzyme converts pyrophosphate into ATP which in turn catalyzes the conversion of luciferin to oxyluciferin which results in the generation of visible light that is then detected by a camera.

In SOLiD sequencing, the molecule to be sequenced is fragmented and used to prepare a population of clonal magnetic beads (in which each bead is conjugated to a plurality of copies of a single fragment) with an adaptor sequence and alternatively a barcode sequence. The beads are bound to a glass surface. Sequencing is then performed through 2-base encoding.

In massively parallel sequencing, randomly fragmented DNA is attached to a surface. The fragments are extended and bridge amplified to create a flow cell with clusters, each with a plurality of copies of a single fragment sequence. The templates are sequenced by synthesizing the fragments in parallel. Bases are indicated by the release of a fluorescent dye correlating to the addition of the particular base to the fragment.

Indirect methods of detecting a marker generally involve assessing the expression of material created from a genomic DNA template such as a RNA or protein molecule. Such expression may be assessed by any of a number of methods used currently in the art and yet to be developed. Examples include any nucleic acid detection method including the following non-limiting examples, microarray RNA analysis, RNA in situ hybridization, RNAse protection assay, Northern blot, reverse transcription PCR, and quantitative reverse transcription PCR. Other examples include any process of detecting expression that uses an antibody including the following non-limiting examples, flow cytometry, immunohistochemistry, ELISA, Western blot, Northwestern blot, and immunoaffinity chromatography. Antibodies may be monoclonal, polyclonal, or any antibody fragment including an Fab, $F(ab)_2$, Fv, scFv, phage display antibody, peptibody, multispecific ligand, or any other reagent with specific binding to a target. Other methods of assessing protein expression include the following non-limiting examples: HPLC, mass spectrometry, protein microarray analysis, PAGE analysis, isoelectric focusing, 2-D gel electrophoresis, and enzymatic assays.

A reagent may be any substance that facilitates any method of detecting a marker. Examples of reagents include nucleic acids such as oligonucleotide probes, nucleic acid mixtures, or full length nucleic acids; proteins such as antibodies, natural ligands, or enzymes; or small molecule compounds in or out of solution such as drugs, buffers, vitamins, or any other artificial or naturally occurring compound that may facilitate the detection of a marker. A reagent may be capable of specific binding to the marker such as a nucleic acid probe or antibody with specificity for the marker.

A reagent may be added to a sample by any of a number of methods including manual methods, mechanical methods, or any combination thereof. The presence of the marker may be signified by any of a number of methods including amplification of a specific nucleic acid sequence, sequencing of a native or amplified nucleic acid, or the detection of a label either bound to or released as a result of the detection of the marker. Addition of a reagent capable of specifically binding a marker to a sample also encompasses addition of the reagent to a sample in which the marker to which the nucleic acid has specificity is absent.

In some aspects of the invention, the presence of a marker may be established by binding to a microarray such as a DNA chip. Examples of DNA chips include chips in which a number of single stranded oligonucleotide probes are affixed to a solid substrate such as silicon glass. Oligonucleotides capable of binding to a marker are capable of hybridizing to all or part of the marker to the exclusion of sequences that differ from those included within the marker by one or more nucleotides. The number of nucleotide differences that may be tolerated are dependent upon the hybridization conditions. Labeled sample DNA is hybridized to the oligonucleotides and detection of the label is correlated with binding of the sample and consequently the presence of the allele in the sample.

In allele-specific hybridization, oligonucleotide sequences representing all possible variations at a polymorphic site are included on a chip. The chip and sample are subject to conditions under which the labeled sample DNA will bind only to an oligonucleotide with an exact sequence match. In allele-specific primer extension, sample DNA hybridized to the chip may be used as a synthesis template with the affixed oligonucleotide as a primer. Under this method, only the added dNTP's are labeled. Incorporation of the labeled dNTP then serves as the signal indicating the presence of the allele. The fluorescent label may be detected by any of a number of instruments configured to read at least four different fluorescent labels on a DNA chip. In another alternative, the identity of the final dNTP added to the oligonucleotide may be assessed by mass spectrometry. In this alternative, the dNTP's may, but need not be labeled with a label of known molecular weight.

A reagent may be affixed to a substrate. In other aspects of the invention, a sample may be affixed to the substrate and made available to a reagent in solution. A reagent or sample may be covalently bound to the substrate or it may be bound by some non-covalent interaction including electrostatic, hydrophobic, hydrogen bonding, Van Der Waals, magnetic, or any other interaction by which a reagent capable of specific binding to a marker such as an oligonucleotide probe may be attached to a substrate while maintaining its ability to recognize the marker to which it has specificity. A substrate may be any solid or semi-solid material onto which a probe may be affixed, attached or printed, either singly or in the presence of one or more additional probes or samples as is exemplified in a microarray. Examples of substrate materials include but are not limited to polyvinyl, polystyrene, polypropylene, polyester or any other plastic, glass, silicon dioxide or other silanes, hydrogels, gold, platinum, microbeads, micelles and other lipid formations, nitrocellulose, or nylon membranes. The substrate may take any form, including a spherical bead or flat surface. For example, the probe may be bound to a substrate in the case of an array or an in situ PCR reaction. The sample may be bound to a substrate in the case of a Southern Blot.

A reagent may include a label. A label may be any substance capable of aiding a machine, detector, sensor, device, or enhanced or unenhanced human eye from differentiating a labeled composition from an unlabeled composition. Examples of labels include but are not limited to: a radioactive isotope or chelate thereof, dye (fluorescent or nonfluorescent) stain, enzyme, or nonradioactive metal. Specific examples include but are not limited to: fluorescein, biotin, digoxigenin, alkaline phosphatase, biotin, streptavidin, $^{3}H$, $^{14}C$, $_{32}P$, $^{35}S$, or any other compound capable of emitting radiation, rhodamine, 4-(4'-dimethylamino-phenylazo)benzoic acid ("Dabcyl"); 4-(4'-dimethylamino-phenylazo)sulfonic acid (sulfonyl chloride) ("Dabsyl"); 5-((2-aminoethyl)-amino)-naphtalene-1-sulfonic acid ("EDANS"); Psoralene derivatives, haptens, cyanines, acridines, fluorescent rhodol derivatives, cholesterol derivatives; ethylenediaminetetraaceticacid ("EDTA") and derivatives thereof or any other compound that may be differentially detected. The label may also include one or more fluorescent dyes optimized for use in genotyping. Examples of such dyes include but are not limited to: FAM, dR110, 5-FAM, 6FAM, dR6G, JOE, HEX, VIC, TET, dTAMRA, TAMRA, NED, dROX, PET, BHQ+, Gold540, and LIZ.

A nucleotide is an individual deoxyribonucleotide or ribonucleotide base. Examples of nucleotides include but are not limited to: adenine, thymine, guanine, cytosine, and uracil, which may be abbreviated as A, T, G, C, or U in representations of oligonucleotide or polynucleotide sequence. Any molecule of two or more nucleotide bases, whether DNA or RNA, may be termed a nucleic acid.

A nucleic acid reagent may be affixed to a solid substrate. Alternatively, the sample may be affixed to a solid substrate and the oligonucleotide placed into a mixture. For example, the nucleic acid reagent may be bound to a substrate in the case of an array or the sample may be bound to a substrate as the case of a Southern Blot, Northern blot or other method that affixes the sample to a substrate. A nucleic acid reagent or sample may be covalently bound to the substrate or it may be bound by some non-covalent interaction including electrostatic, hydrophobic, hydrogen bonding, Van Der Waals, magnetic, or any other interaction by which an oligonucleotide may be attached to a substrate while maintaining its ability to recognize the allele to which it has specificity. A substrate may be any solid or semi-solid material onto which a probe may be affixed, attached or printed, either singly or in the formation of a microarray. Examples of substrate materials include but are not limited to polyvinyl, polystyrene, polypropylene, polyester or any other plastic, glass, silicon dioxide or other silanes, hydrogels, gold, platinum, microbeads, micelles and other lipid formations, nitrocellulose, or nylon membranes. The substrate may take any shape, including a spherical bead or flat surface.

Nucleic acid amplification may be performed using nucleic acids from any source. In general, nucleic acid amplification is a process by which copies of a nucleic acid may be made from a source nucleic acid. In some nucleic amplification methods, the copies are generated exponentially. Examples of nucleic acid amplification include but are not limited to: the polymerase chain reaction (PCR), ligase chain reaction (LCR) self-sustained sequence replication (3SR), nucleic acid sequence based amplification (NASBA) strand displacement amplification (SDA) amplification with Qβ replicase, whole genome amplification with enzymes such as φ29, whole genome PCR, in vitro transcription with Klenow or any other RNA polymerase, or any other method by which copies of a desired sequence are generated.

Polymerase chain reaction (PCR) is a particular method of amplifying DNA, generally involving the mixing of a nucleic sample, two or more primers, a DNA polymerase, which may be a thermostable DNA polymerase such as Taq or Pfu, and deoxyribose nucleoside triphosphates (dNTP's). In general, the reaction mixture is subjected to temperature cycles comprising a denaturation stage, (typically 80-100° C.) an annealing stage with a temperature that may be based on the melting temperature (Tm) of the primers and the degeneracy of the primers, and an extension stage (for example 40-75° C.) In real-time PCR analysis, additional reagents, methods, optical detection systems, and devices are used that allow a measurement of the magnitude of fluorescence in proportion to concentration of amplified DNA. In such analyses, incorporation of fluorescent dye into the amplified strands may be detected or labeled probes that bind to a specific sequence during the annealing phase release their fluorescent tags during the extension phase. Either of these will allow a quantification of the amount of specific DNA present in the initial sample. RNA may be detected by PCR analysis by creating a DNA template from RNA through a reverse transcriptase enzyme. In some aspects of the invention, the marker may be detected by quantitative PCR analysis, which may be performed using a kit containing components that facilitate genotyping analysis. Genotyping analysis may be performed using a probe that is capable of hybridizing to a nucleic acid sequence of interest.

An oligonucleotide is a reagent capable of binding a nucleic acid sequence. An oligonucleotide may be any polynucleotide of at least 2 nucleotides. Oligonucleotides may be less than 10, less than 15, less than 20, less than 30, less than 40, less than 50, less than 75, less than 100, less than 200, less than 500, or more than 500 nucleotides in length. While oligonucleotides are often linear, they may, depending on their sequence and conditions, assume a two- or three-dimensional structure. Oligonucleotides may be chemically synthesized by any of a number of methods including sequential synthesis, solid phase synthesis, or any other synthesis method now known or yet to be disclosed. Alternatively, oligonucleotides may be produced by recombinant DNA based methods. One skilled in the art would understand the length of oligonucleotide necessary to perform a particular task. Oligonucleotides may be directly labeled, used as primers in PCR or sequencing reactions, or bound directly to a solid substrate as in oligonucleotide arrays.

Oligonucleotide synthesis is the chemical synthesis of oligonucleotides with a defined chemical structure and/or nucleic acid sequence by any method now known in the art or yet to be disclosed. Oligonucleotide synthesis may be carried out by the addition of nucleotide residues to the 5'-terminus of a growing chain. Elements of oligonucleotide synthesis include: De-blocking: A DMT group is removed with a solution of an acid, such as TCA or Dichloroacetic acid (DCA), in an inert solvent (dichloromethane or toluene) and washed out, resulting in a free 5' hydroxyl group on the first base. Coupling: A nucleoside phosphoramidite (or a mixture of several phosphoramidites) is activated by an acidic azole catalyst, tetrazole, 2-ethylthiotetrazole, 2-bezyl-thiotetrazole, 4,5-dicyanoimidazole, or a number of similar compounds. This mixture is brought in contact with the starting solid support (first coupling) or oligonucleotide precursor (following couplings) whose 5'-hydroxy group reacts with the activated phosphoramidite moiety of the incoming nucleoside phosphoramidite to form a phosphite triester linkage. The phosphoramidite coupling may be carried out in anhydrous acetonitrile. Unbound reagents and by-products may be removed by washing. Capping: A small percentage of the solid support-bound 5'-OH groups (0.1 to 1%) remain unreacted and should be permanently blocked from further chain elongation to prevent the formation of oligonucleotides with an internal base deletion commonly referred to as (n-1) shortmers. This is done by acetylation of the unreacted 5'-hydroxy groups using a mixture of acetic anhydride and 1-methylimidazole as a catalyst. Excess reagents are removed by washing. Oxidation: The newly formed tricoordinated phosphite triester linkage is of limited stability under the conditions of oligonucleotide synthesis. The treatment of the support-bound material with iodine and water in the presence of a weak base (pyridine, lutidine, or collidine) oxidizes the phosphite triester into a tetracoordinated phosphate triester, a protected precursor of the naturally occurring phosphate diester internucleosidic linkage. This step can be substituted with a sulfurization step to obtain oligonucleotide phosphorothioates. In the latter case, the sulfurization step is carried out prior to capping. Upon the completion of the chain assembly, the product may be released from the solid phase to solution, deprotected, and collected. Products may be isolated by HPLC to obtain the desired oligonucleotides in high purity.

Some aspects of the invention include the use of one or more oligonucleotides. For example, the oligonucleotides can include the following sequences: AGACTGTCCCAAT-GTCAAGCTTTC (SEQ ID NO: 1), GCCTTGTATGTGG-TAACACCAGTG (SEQ ID NO: 2), GWGCCTTGTAT-GTGGTAACACCAGTA (SEQ ID NO: 3), AGACTGTCCCAATGTCAAGCTTTC (SEQ ID NO: 4), ATTAACCTTAGTGTTGGAGACCTTGACT (SEQ ID NO: 5), AACCTTAGTGTTGGAGACCTTGACA (SEQ ID NO: 6), CCCAGCAACCTTGATCTGGA (SEQ ID NO: 7), AGCTGCTCTAAGAGACACATCATCA (SEQ ID NO: 8), AGCTGCTCTAAGAGACACATCATCC (SEQ ID NO: 9), AATCGCTCGTCCTCATATGACA (SEQ ID NO: 10), GTAGGCGGTGGGATAAGGTG (SEQ ID NO: 11), GGTAGGCGGTGGGATAAGGTA (SEQ ID NO: 12), CGTTAATTTGGTTGTTTGACAACCT (SEQ ID NO: 13), AGCAACTCACGCAGAAACAGAC (SEQ ID NO: 14), GAGCAACTCACGCAGAAACAGAT (SEQ ID NO: 15), TGACATTGGGACAGTCTGCAAT (SEQ ID NO: 16), ACTGCTGCTTCTCCCGTTGT (SEQ ID NO: 17), CTGCTGCTTCTCCCGTTGA (SEQ ID NO: 18), ACCCA-GTCATTAACCTTAGTGTTGGA (SEQ ID NO: 19), CTCGTTCGTCAAYCACGTTAGA (SEQ ID NO: 20), and/or TCGTTCGTCAAYCACGTTAGC (SEQ ID NO: 21). As described in greater detail herein, these one or more mixtures of these oligonucleotides can be used in detecting and/or determining a genotype of C. gattii.

Moreover, in some aspects, the oligonucleotides with degenerate sequences may also be supplied as an oligonucleotide mixture with nucleotides meeting the conditions set by the degenerate primer sequence. For example, a primer mixture including SEQ ID NO: 3 may include oligonucleotides of GAGCCTTGTATGTGGTAACACCAGTA (SEQ ID NO: 22) and GTGCCTTGTATGTGGTAACACCAGTA (SEQ ID NO: 23). A primer mixture including SEQ ID NO: 20 may include oligonucleotides CTCGTTCGTCAACCACGTTAGA (SEQ ID NO: 24) and CTCGTTCGTCAATCACGTTAGA (SEQ ID NO: 25). A primer mixture including SEQ ID NO: 21 may include oligonucleotides TCGTTCGTCAACCACGTTAGC (SEQ ID NO: 26) and TCGTTCGTCAATCACGTTAGC (SEQ ID NO: 27).

Kits that facilitate methods of detecting a marker may include one or more of the following reagents: specific nucleic acids such as oligonucleotides, labeling reagents, enzymes including PCR amplification reagents such as the thermostable DNA polymerases Taq or Pfu, reverse transcriptase, or one or more other polymerases, and/or reagents that facilitate hybridization. Specific nucleic acids may include nucleic acids, polynucleotides, oligonucleotides (DNA, or RNA), or any combination of molecules that includes one or more of the above, or any other molecular entity capable of specific binding to a nucleic acid marker. In one aspect of the invention, the specific nucleic acid comprises one or more oligonucleotides capable of hybridizing to the marker.

A kit may also contain an indication of a result of the use of the kit that signifies a particular characteristic. An indication includes any guide to a result that would signal the presence or absence of any characteristic that the kit is configured to predict. For example, the indication may be expressed numerically, expressed as a color or density of a color, expressed as an intensity of a band, derived from a standard curve, or expressed in comparison to a control. The indication may be communicated through the use of a writing. A writing may be any communication of the result in a tangible medium of expression. The writing may be contained physically in or on the kit (on a piece of paper for example), posted on the Internet, mailed to the user separately from the kit, or embedded in a software package. The writing may be in any medium that communicates how the result may be used to predict the cellular or physiological characteristic that the kit is intended to predict, such as a printed document, a photograph, sound, color, or any combination thereof.

It should be understood from the foregoing that, while particular embodiments have been illustrated and described, various modifications can be made thereto without departing from the spirit and scope of the invention as will be apparent to those skilled in the art. Such changes and modifications are within the scope and teachings of this invention as defined in the claims appended hereto.

EXAMPLES

Materials and Methods
SYBR MAMA Design

MAMA primers have an intentional penultimate mismatch nucleotide at the 3' end; the ultimate base is always the SNP assay target and is a perfect match for the target SNP [18]. Mismatches decrease the efficiency of primer extension by Taq polymerase, such that if two mismatches are found together under the 3' end of the primer, the efficiency of the PCR is significantly reduced. However, if a single mismatch at the penultimate base is present, extension occurs from the 3' matched base, and efficiency of the PCR remains relatively high. Fluorogenic oligonucleotide probes are not needed to discriminate SNPs with this method. This discriminatory design results in a cost-efficient, powerful and simple method of SNP genotyping [17, 21]. Separate PCR reactions are performed with a MAMA primer specific for only one of the two target SNPs and with one universal primer for amplification from the alternate direction. Comparison of cycle threshold (Ct) values will reveal which reaction is more efficient (has the smaller Ct value). The more efficient reaction corresponds to the SNP that is present in the sample.

MAMA Design for MLST Groups VGI, VGII, VGIII, and VGIV

The MLST SYBR MAMA design was informed by MLST data collected for 202 C. gatii strains from a worldwide collection [20]. The MLST library included sequences from 77, 75, 26, and 24 isolates of the VGI, VGII, VGIII, VGIV molecular types, respectively. The gene encoding mannitol-1-phosphate dehydrogenase (MPD1) was selected as the best candidate for assay design based on its sequence conservation within each of the four molecular types that allowed for design of assay primers with a minimum number of degenerate bases. All 15 of the known MPD1 allele sequences were aligned with SeqMan Pro v.9.0.4 (DNASTAR, Madison, Wis.). SNPs specific for each of the molecular types were identified in the sequence alignment. MAMA primers were manually designed in Primer Express 3.0 (Life Technologies, Carlsbad, Calif.) software with optimal mismatches chosen as suggested by Li et. al. [19] (Table 1).

MAMA Design for VGIIa, VGIIb, and VGIIc Subtypes

Whole genome sequence typing (WGST) analysis of 20 C. gattii strains from a previous study revealed canonical SNPs specific for each of the VGII a, b and c subtypes (n=2720, 3547, and 3819, respectively) [9]. In order to minimize interference of adjacent mutations with primer design, the genotype-specific SNPs were sorted according to nearest neighboring mismatch within the sequence alignment; in short, the SNPs with the most-conserved flanking regions were the top candidates for assay design. Sequence from the R265 strain reference genome [GenBank: CH408164] [2] surrounding the genotype-specific SNPs was used for assay design. SYBR MAMA primers were designed using the same criteria as previously described for the MLST MAMA (Table 1).

Isolate Selection

Initially, assays were validated with genomic DNA extracted from 57 C. gattii strains of North American origin and some historical isolates. The panel of isolates including: 13 VGIIa, 4 VGIIb, and 24 VGIIc, and 8 each of VGI and VGIII, was analyzed using each of the assays (Table 2). All DNAs were genotyped by MLST prior to screening. Further validation of the assays was accomplished by employing a more diverse isolate collection of 55 strains including isolates of international origin; this panel was comprised of 10 VGI, 10 VGIIa, 9 VGIIb, 8 VGIIc, 8 VGIII, and 10 VGIV molecular types (Table 3). The strains came from a variety of environmental, human and animal sources, including cats, a dog, an alpaca, a porpoise, a Sheep and a Cow.

Isolate Culturing and DNA Extraction

Isolates were grown on Yeast Peptone Glucose (YPD) agar plus 0.5% NaCl at 37° C. for 24 hours; and DNA was prepared using an UltraClean DNA Isolation Kit as described by the manufacturer, with some modifications (MO BIO Laboratories, Carlsbad, Calif.). Briefly, ~0.5 grams of microbial cells were suspended in lysis solution in a MicroBead tube and heated to 65° C. for 15 minutes to increase lysis efficiency. The MicroBead tube was then secured horizontally using the MO BIO vortex adapter tube holder (MO BIO Laboratories, Carlsbad, Calif.) and vortexed at maximum speed for 10 minutes; post cell lysis, microtubes were immediately placed on ice for 5 minutes. After the lysis steps, DNA extraction was completed per manufacturer's instructions. DNA was stored at −20° C.

Real-Time PCR

Real-time PCR was performed on the ABI 7900HT real-time PCR System (Life Technologies, Carlsbad, Calif.). Reactions for both perfect match and mismatch primer sets were conducted in separate wells of a 384-well optical plate, and reactions for each primer set were run in triplicate. Reactions were 10 µL total volume composed of 1× Platinum SYBR Green qPCR SuperMix-UDG with ROX (Invitrogen, Grand Island, N.Y.), 200 nM each of forward and reverse primers, and 1 µL DNA extract (diluted 1:10). Reactions were incubated for 3 min at 50° C. for UDG digest followed by 3 min at 95° C. for Taq polymerase activation. PCR consisted of 45 cycles of 15 s at 95° C. for denaturation followed by 1 min at 60° C. annealing and extension. Dissociation of PCR product was performed for 15 sec at 95° C., 15 sec at 60° C. and 15 sec at 95° C. as a quality assurance step to inspect reactions for primer-dimer. Dissociation curves were not used for isolate genotyping, rather to ensure amplification was specific for the targeted sequence and to preclude non-specific amplification associated with the ability of SYBR Green chemistry to bind any double-stranded DNA. Data were analyzed in Sequence Detection Systems 2.3 software (Life Technologies, Carlsbad, Calif.) for calculation of cycle threshold (Ct) values and interpretation of dissociation curves.

For MAMA results, the perfect match primer set will amplify earlier and yield the lowest Ct value, corresponding to the SNP genotype of the isolate; secondary delayed amplification plots with a higher Ct value, if present, are due to mismatch priming (FIG. 1, including A, B, and C). An algorithm for genotype calling was implemented to expedite data analysis. The delta Ct value was calculated by subtracting the match primer mean Ct from the mismatch primer mean Ct. If the mismatch priming fails to yield a Ct value because it is beyond the instrument range, a Ct value=40 is assigned in order to calculate a ΔCt.

$$\Delta Ct = (\text{mismatch mean } Ct) - (\text{perfect match mean } Ct) \qquad (01)$$

A negative ΔCt value indicates a mismatch allele, whereas a positive ΔCt indicates a match allele. A stringent threshold of |ΔCt|≥3.3, approximately equivalent to one $\log_{10}$ difference in the dynamic range, was established to ensure accuracy of allele calls. If |ΔCt|<3.3 is below the stringent threshold, this could result in an inaccurate genotype call. In this case, it is advisable to re-screen the sample across the failed assays.

Sensitivity and specificity of the assay panel were calculated as well as concordance with the known MLST type as determined by sequencing the MLST house keeping genes. Assay repeatability and reproducibility were tested by screening nine replicate reactions with the matching primer sets and DNA for each assay on three separate days. The lower limit of detection for each assay and its matching template pair was tested. Each matching template and assay pair was tested using six $\log_{10}$ serial dilutions of a single template DNA, starting with 0.5 ng/µl. Template DNA was quantified in triplicate by NanoDrop 3300 fluorospectrometer (NanoDrop Technologies, Wilmington, Del.) using Quant-iT PicoGreen dsDNA Reagent (Life Technologies, Carlsbad, Calif.), according to manufacturer's instructions. Real-time PCR reactions were performed in triplicate for each dilution.

Results

Initial validation revealed the assay panel was 100% sensitive; each assay appropriately identified the known isolate genotypes. The ΔCt values for our validation panel confirmed the stringent threshold ΔCt=3.3 sufficient to discriminate the genotypes. In addition, the assay panel was 100% specific; no cross reactivity occurred between assays and non-matching genotypes. Further validation of the assay panel with additional strains revealed 100% sensitivity and specificity. A total of 112 strains were screened across the MLST assay panel and 100% sensitivity and specificity was observed (Table 4). A total of 68 previously genotyped strains were screened across the VGII subtyping assay panel with 100% sensitivity and specificity (Table 5). The assay coefficients of variation ranged from 0.22% to 4.33% indicating high assay repeatability and reproducibility within and between runs (Table 6). The assays were designed for genotyping of DNA from known *C. gattii* isolates, and are not validated for application to clinical specimens; they were able to detect DNA concentrations as low as 0.5 pg/µl (Table 7).

*C. gattii* is an emerging pathogen in the US Pacific Northwest and British Columbia. Molecular and epidemiological investigations revealed the Vancouver Island, BC outbreak was attributed to a novel and seemingly hypervirulent VGIIa genotype [7,20,22]; moreover, the recent PNW outbreak was attributed to an additional novel genotype, VGIIc [23]. These apparent new genotypes (VGIIa and VGIIc), are responsible for greater than 90% of *C. gattii* infections in the BC/PNW region [7]. Given the increased virulence, varying antifungal susceptibilities and clinical outcomes caused by these genotypes, as compared to other *C. gattii* genotypes, it will be useful to conduct regular genotyping of *C. gattii* isolates for both clinical and epidemiological response purposes [5,7,9,16].

Disclosed herein is a MAMA real-time PCR panel for cost-efficient and rapid genotyping of *C. gattii* molecular types (I-IV) and VGII subtypes (a-c) as a means to better understand genotype distribution of *C. gattii* in North America. To validate the assays, DNA from a diverse North American and international isolate collection of *C. gattii* isolates from human, environmental, and animal sources. All DNA had been previously typed by MLST. The assay panel performed with 100% sensitivity and specificity and was 100% concordant with MLST results. The VGII subtype specific assays may be more pertinent to the North American public health and medical communities; the molecular type (I-IV) specific assays will be useful for both North American and global genotyping. The assay is designed for screening in a cost-effective, step-wise manner. The molecular type-specific assays should be performed first on all isolates. In North America, the VGIV assay can be withheld for the first screen, as isolates of this molecular type have not yet been isolated from North America. For those North American isolates that are VGII by molecular type, the subtype-specific assays should be performed for typing VGIIa, VGIIb, or VGIIc. As we further our understanding of *C. gattii* populations around the world and their genotype-phenotype relationships, additional subtype specific assays can be similarly developed for local and global research purposes.

The following references are hereby incorporated by reference in their entireties for any purpose:

1. Boyers M, Hagen F, Boekhout T: Diversity of the *Cryptococcus neoformans-Cryptococcus gattii* species complex. *Rev Iberoam Micol* 2008, 25(1):S4-S12.
2. D'Souza C A, Kronstad J W, Taylor G, Warren R, Yuen M, Hu G, Jung W H, Sham A, Kidd S E, Tangen K, Lee N, Zeilmaker T, Sawkins J, McVicker G, Shah S, Gnerre S, Griggs A, Zeng Q, Bartlett K, Li W, Wang X, Heitman J, Stajich J E, Fraser J A, Meyer W, Carter D, Schein J, Krzywinski M, Kwon-Chung K J, Varma A, et al.: Genome variation in *Cryptococcus gattii*, an emerging pathogen of immunocompetent hosts. *MBio* 2011, 2:e00342-10.
3. Lockhart S R, Iqbal N, Bolden C B, DeBess E E, Marsden-Haug N, Worhle R, Thakur R, Harris J R: Epidemiologic cutoff values for triazole drugs in *Cryptococcus gattii*: correlation of molecular type and in vitro susceptibility. *Diagn Microbiol Infect Dis* 2012, 73(2): 144-148.

4. Stephen C S L, Black W, Fyfe M, Raverty S: Multispecies outbreak of cryptococcosis on southern Vancouver Island, British Columbia. *Can Vet J* 2002, 43(10):792-794.
5. Iqbal N, DeBess E E, Wohrle R, Sun B, Nett R J, Ahlquist A M, Chiller T, Lockhart S R: Correlation of genotype and in vitro susceptibilities of *Cryptococcus gattii* strains from the Pacific Northwest of the United States. *J Clin Microbiol* 2010, 48(2):539-544.
6. Byrnes E J 3rd, Bildfell R J, Frank S A, Mitchell T G, Marr K A, Heitman J: Molecular evidence that the range of the Vancouver Island outbreak of *Cryptococcus gattii* infection has expanded into the Pacific Northwest in the United States. *J Infect Dis* 2009, 199(7):1081-1086.
7. Byrnes E J 3rd, Li W, Lewit Y, Ma H, Voelz K, Ren P, Carter D A, Chaturvedi V, Bildfell R J, May R C, Heitman J: Emergence and pathogenicity of highly virulent *Cryptococcus gattii* genotypes in the northwest United States. *PLoS Pathog* 2010, 6(4):e1000850.
8. Walraven C J, Gerstein W, Hardison S E, Wormley F, Lockhart S R, Harris J R, Fothergill A, Wickes B, Gober-Wilcox J, Massie L, Ku T S, Firacative C, Meyer W, Lee S A: Fatal disseminated *Cryptococcus gattii* infection in New Mexico. *PLoS One* 2011, 6(12):e28625.
9. Gillece J D, Schupp J M, Balajee S A, Harris J, Pearson T, Yan Y, Keim P, DeBess E, Marsden-Haug N, Wohrle R, Engelthaler D M, Lockhart S R: Whole genome sequence analysis of *Cryptococcus gattii* from the Pacific Northwest Reveals unexpected diversity. *PLoS One* 2011, 6(12):e28550.
10. Hagen F, Illnait-Zaragozi M T, Bartlett K H, Swinne D, Geertsen E, Klaassen C H, Boekhout T, Meis J F: In vitro antifungal susceptibilities and amplified fragment length polymorphism genotyping of a worldwide collection of 350 clinical, veterinary, and environmental *Cryptococcus gattii* isolates. *Antimicrob Agents Chemother* 2010, 54(12):5139-5145.
11. Sidrim J J, Costa A K, Cordeiro R A, Brilhante R S, Moura F E, Castelo-Branco D S, Neto M P, Rocha M F: Molecular methods for the diagnosis and characterization of *cryptococcus*: a review. *Can J Microbiol* 2010, 56(6): 445-458.
12. Firacative C T L, Meyer W: MALDI-TOF MS enables the rapid identification of the major molecular types within the *Cryptococcus neoformans/C. Gattii* species complex. *PLoS One* 2012, 7(5):e37566.
13. Posteraro B, Vella A, Cogliati M, De Carolis E, Florio A R, Posteraro P, Sanguinetti M, Tortorano A M: Matrix-assisted laser desorption ionization-time of flight mass spectrometry-based method for discrimination between molecular types of *Cryptococcus neoformans* and *Cryptococcus gattii*. *J Clin Microbiol* 2012, 50(7):2472-2476.
14. Hanafy A, Kaocharoen S, Jover-Botella A, Katsu M, Iida S, Kogure T, Gonoi T, Mikami Y, Meyer W: Multilocus microsatellite typing for *Cryptococcus neoformans* var. *grubii*. *Med Mycol* 2008, 46(7):685-696.
15. Gago S, Zaragoza O, Cuesta I, Rodriguez-Tudela J L, Cuenca-Estrella M, Buitrago M J: High-resolution melting analysis for identification of the *Cryptococcus neoformans-Cryptococcus gattii* complex. *J Clin Microbiol* 2011, 49(10):3663-3666.
16. Meyer W, Aanensen D M, Boekhout T, Cogliati M, Diaz M R, Esposto M C, Fisher M, Gilgado F, Hagen F, Kaocharoen S, Litvintseva A P, Mitchell T G, Simwami S P, Trilles L, Viviani M A, Kwon-Chung J: Consensus multi-locus sequence typing scheme for *Cryptococcus neoformans* and *Cryptococcus gattii*. *Med Mycol* 2009, 47(6):561-570.
17. Birdsell D N, Pearson T, Price E P, Hornstra H M, Nera R D, Stone N, Gruendike J, Kaufman E L, Pettus A H, Hurbon A N, Buchhagen J L, Harms N J, Chanturia G, Gyuranecz M, Wagner D M, Keim P S: Melt analysis of mismatch amplification mutation assays (Melt-MAMA): a functional study of a cost-effective SNP genotyping assay in bacterial models. *PLoS One* 2012, 7(3):e32866.
18. Cha R S, Zarbl H, Keohavong P, Thilly W G: Mismatch amplification mutation assay (MAMA): application to the c-H-ras gene. *Genome Res* 1992, 2(1):14-20.
19. Li B, Kadura I, Fu D-J, Watson D E: Genotyping with TaqMAMA. *Genomics* 2004, 83(2):311-320.
20. Fraser J A, Giles S S, Wenink E C, Geunes-Boyer S G, Wright J R, Diezmann S, Allen A, Stajich J E, Dietrich F S, Perfect J R, Heitman J: Same-sex mating and the origin of the Vancouver Island *Cryptococcus gattii* outbreak. *Nature* 2005, 437(7063):1360-1364.
21. Liu C M, Driebe E M, Schupp J, Kelley E, Nguyen J T, McSharry J J, Weng Q, Engelthaler D M, Keim P S: Rapid quantification of single-nucleotide mutations in mixed influenza A viral populations using allele-specific mixture analysis. *J Virol Methods* 2010, 163(1):109-115.
22. Kidd S E, Hagen F, Tscharke R L, Huynh M, Bartlett K H, Fyfe M, Macdougall L, Boekhout T, Kwon-Chung K J, Meyer W: A rare genotype of *Cryptococcus gattii* caused the cryptococcosis outbreak on Vancouver Island (British Columbia, Canada). *Proc Natl Acad Sci USA* 2004, 101(49):17258-17263.
23. Silva D C, Martins M A, Szeszs M W, Bonfietti L X, Matos D, Melhem M S: Susceptibility to antifungal agents and genotypes of Brazilian clinical and environmental *Cryptococcus gattii* strains. *Diagn Microbiol Infect Dis* 2012, 72(4):332-339.
Kelley, E J et al., Real-time PCR assays for genotyping of *Cryptococcus gattii* in North America. *BMC Microbiology* 2014, 14:125.

TABLE 1

MAMA real-time PCR assay sequences and targets for genotyping *C. gatii*.

| Genotype | Assay Name | Gene (SNP position) | Base call match/ mismatch | Universal Primer sequence 5' --> 3' | Match MAMA Primer sequence 5' --> 3' | Mismatch MAMA Primer sequence 5' --> 3' |
|---|---|---|---|---|---|---|
| VGI | VGI-MPD471 | MPD1 (471) | G/A | AGACTGTCCCAATGTC AAGCTTTC SEQ ID NO: 1 | GCCTTGTATGTGGTAAC ACCAGTG SEQ ID NO: 2 | GWGCCTTGTATGTGG TAACACCAGTA SEQ ID NO: 3 |
| VGII | VGII-MPD495 | MPD1 (495) | T/A | AGACTGTCCCAATGTC AAGCTTTC SEQ ID NO: 4 | ATTAACCTTAGTGTTGG AGACCTTGACT SEQ ID NO: 5 | AACCTTAGTGTTGGA GACCTTGACA SEQ ID NO: 6 |

TABLE 1-continued

MAMA real-time PCR assay sequences and targets for genotyping *C. gatii*.

| Genotype | Assay Name | Gene (SNP position) | Base call match/mismatch | Universal Primer sequence 5' --> 3' | Match MAMA Primer sequence 5' --> 3' | Mismatch MAMA Primer sequence 5' --> 3' |
|---|---|---|---|---|---|---|
| VGIIa | VGIIa-45211 | hypothetical protein | A/C | CCCAGCAACCTTGATCTGGA SEQ ID NO: 7 | AGCTGCTCTAAGAGACACATCATCA SEQ ID NO: 8 | AGCTGCTCTAAGAGACACATCATCC SEQ ID NO: 9 |
| VGIIb | VGIIb-502129 | not annotated | G/A | AATCGCTCGTCCTCATATGACA SEQ ID NO: 10 | GTAGGCGGTGGGATAAGGTG SEQ ID NO: 11 | GGTAGGCGGTGGGATAAGGTA SEQ ID NO: 12 |
| VGIIc | VGIIc-257655 | non-coding region | C/T | CGTTAATTTGGTTGTTTGACAACCT SEQ ID NO: 13 | AGCAACTCACGCAGAAACAGAC SEQ ID NO: 14 | GAGCAACTCACGCAGAAACAGAT SEQ ID NO: 15 |
| VGIII | VGIII-MPD198 | MPD1 (198) | T/A | TGACATTGGGACAGTCTGCAAT SEQ ID NO: 16 | ACTGCTGCTTCTCCCGTTGT SEQ ID NO: 17 | CTGCTGCTTCTCCCGTTGA SEQ ID NO: 18 |
| VGIV | VGIV-MPD423 | MPD1 (423) | A/C | ACCCAGTCATTAACCTTAGTGTTGGA SEQ ID NO: 19 | CTCGTTCGTCAAYCACGTTAGA SEQ ID NO: 20 | TCGTTCGTCAAYCACGTTAGC SEQ ID NO: 21 |

TABLE 2

*C. gattii* strains for initial assay validation

| Isolate ID | MLST | Year | Geographic origin | Source |
|---|---|---|---|---|
| B7488 | VGI | 2009 | Oregon | Human |
| B7496 | VGI | 2009 | Hawaii | Dolphin |
| B8551 | VGI | 2010 | Oregon | Human |
| B8852 | VGI | 2010 | Oregon | Human |
| B8886 | VGI | 2010 | Oregon | Soil |
| B8887 | VGI | 2010 | Oregon | Soil |
| B8990 | VGI | 2010 | California | Human |
| B9009 | VGI | 2011 | Washington | Human |
| B6864 | VGIIa | 2004 | Oregon | Human |
| B7395 | VGIIa | 2008 | Washington | Dog |
| B7422 | VGIIa | 2009 | Oregon | Cat |
| B7436 | VGIIa | 2009 | California | Alpaca |
| B7467 | VGIIa | 2009 | Oregon | Porpoise |
| B8555 | VGIIa | 2006 | Washington | Human |
| B8577 | VGIIa | 2009 | British Columbia | Soil |
| B8793 | VGIIa | 2010 | Oregon | Canine |
| B8849 | VGIIa | 2010 | Oregon | Environmental |
| CA-1014 | VGIIa | unknown | California | Human |
| CBS-7750 | VGIIa | 1990 | California | Environmental |
| ICB-107 | VGIIa | unknown | Brazil | Human |
| NIH-444 | VGIIa | 1972 | Washington | Human |
| B7394 | VGIIb | 2008 | Washington | Cat |
| B7735 | VGIIb | 2009 | Oregon | Human |
| B8554 | VGIIb | 2010 | Oregon | Dog |
| B8828 | VGIIb | 2010 | Washington | Porpoise |
| B6863 | VGIIc | 2005 | Oregon | Human |
| B7390 | VGIIc | 2008 | Idaho | Human |
| B7432 | VGIIc | 2009 | Oregon | Human |
| B7434 | VGIIc | 2008 | Oregon | Human |
| B7466 | VGIIc | 2008 | Oregon | Cat |
| B7491 | VGIIc | 2009 | Oregon | Human |
| B7493 | VGIIc | 2009 | Oregon | Sheep |
| B7641 | VGIIc | 2008 | Oregon | Cat |
| B7737 | VGIIc | 2009 | Oregon | Human |
| B7765 | VGIIc | 2009 | Oregon | Dog |
| B8210 | VGIIc | 2008 | Oregon | Human |
| B8214 | VGIIc | 2009 | Oregon | Human |
| B8510 | VGIIc | 2009 | Oregon | Human |
| B8549 | VGIIc | unknown | Oregon | Human |
| B8552 | VGIIc | unknown | Oregon | Human |
| B8571 | VGIIc | 2009 | Washington | Human |
| B8788 | VGIIc | 2010 | Oregon | Human |
| B8798 | VGIIc | 2005 | Oregon | Human |
| B8821 | VGIIc | 2010 | Oregon | Human |
| B8825 | VGIIc | 2009 | Oregon | Human |
| B8833 | VGIIc | 2010 | Oregon | Cat |
| B8838 | VGIIc | 2010 | Washington | Human |
| B8843 | VGIIc | 2010 | Oregon | Human |
| B8853 | VGIIc | 2010 | Oregon | Cat |
| B7415 | VGIII | 2009 | California | Alpaca |
| B7495 | VGIII | 2009 | California | Human |
| B8212 | VGIII | 2007 | Oregon | Human |
| B8260 | VGIII | 2009 | Washington | Cat |
| B8262 | VGIII | 1992 | California | Human |
| B8516/B8616 | VGIII | 2009 | Oregon | Cat |
| B9143 | VGIII | 2011 | California | Human |
| B9146 | VGIII | 2011 | California | Human |

TABLE 3

*C. gattii* strains for additional assay validation

| Culture collection ID | Geographic origin | Sample type | MLST | Year of isolation |
|---|---|---|---|---|
| B4501 | Australia | Human | VGI | unknown |
| B4503 | Australia | Human | VGI | unknown |
| B4504 | Australia | Human | VGI | unknown |
| B4516 | Australia | Human | VGI | unknown |
| B5765 | India | Environmental | VGI | unknown |
| B9018 | California | Human | VGI | 2011 |
| B9019 | New Mexico | Human | VGI | 2011 |
| B9021 | Rhode Island | Human | VGI | 2011 |
| B9142 | Georgia | Human | VGI | 2011 |
| B9149 | California | Human | VGI | 2011 |
| B8508 | Oregon | Human | VGIIa | 2009 |
| B8512 | Oregon | Alpaca | VGIIa | 2009 |
| B8558 | Washington | Human | VGIIa | 2010 |
| B8561 | Washington | Human | VGIIa | 2010 |
| B8563 | Washington | Human | VGIIa | 2010 |
| B8567 | Washington | Dog | VGIIa | 2010 |
| B8854 | Washington | Human | VGIIa | 2010 |
| B8889 | Oregon | Environmental | VGIIa | 2010 |
| B9077 | Washington | Environmental | VGIIa | 2011 |
| B9296 | British Columbia | Environmental | VGIIa | 2011 |
| B8211 | Oregon | Human | VGIIb | 2009 |

TABLE 3-continued

*C. gattii* strains for additional assay validation

| Culture collection ID | Geographic origin | Sample type | MLST | Year of isolation |
|---|---|---|---|---|
| B8966 | Oregon | Horse | VGIIb | 2010 |
| B9076 | Washington | Environmental | VGIIb | 2011 |
| B9157 | Washington | Horse | VGIIb | 2011 |
| B9170 | Washington | Porpoise | VGIIb | 2011 |
| B9234 | Washington | Cat | VGIIb | 2011 |
| B9290 | British Columbia | Cat | VGIIb | 2011 |
| B9241 | Oregon | Human | VGIIb | 2011 |
| B9428 | Washington | Cat | VGIIb | 2012 |
| B9159 | Washington | Sheep | VGIIc | 2011 |
| B9227 | Oregon | Cat | VGIIc | 2011 |
| B9235 | Oregon | Human | VGIIc | 2011 |
| B9244 | Oregon | Human | VGIIc | 2011 |
| B9245 | Oregon | Human | VGIIc | 2011 |
| B9295 | British Columbia | Environmental | VGIIc | 2011 |
| B9302 | Oregon | Environmental | VGIIc | 2011 |
| B9374 | Oregon | Human | VGIIc | 2011 |
| B8965 | New Mexico | Human | VGIII | 2010 |
| B9148 | California | Human | VGIII | 2011 |
| B9151 | Michigan | Human | VGIII | 2011 |
| B9163 | New Mexico | Human | VGIII | 2011 |
| B9237 | New Mexico | Cat | VGIII | 2011 |
| B9372 | California | Cow | VGIII | 2011 |
| B9422 | Oregon | Cat | VGIII | 2012 |
| B9430 | Alaska | Cat | VGIII | 2012 |
| B7238 | Botswana | Human | VGIV | 2005 |
| B7240 | Botswana | Human | VGIV | 2005 |
| B7243 | Botswana | Human | VGIV | 2005 |
| B7247 | Botswana | Human | VGIV | 2005 |
| B7249 | Botswana | Human | VGIV | 2005 |
| B7260 | Botswana | Human | VGIV | 2006 |
| B7262 | Botswana | Human | VGIV | 2006 |
| B7263 | Botswana | Human | VGIV | 2006 |
| B7264 | Botswana | Human | VGIV | 2006 |
| B7265 | Botswana | Human | VGIV | 2006 |

TABLE 4

MLST SYBR MAMA Ct values and genotype assignments for VGI-VGIV

| Isolate ID | Strain type via MLST | VGI_MPD471 | | | | VGII_MPD495 | | | | VGIII_MPD198 | | | | VGIV_MPD423 | | | | Final Call |
|---|---|---|---|---|---|---|---|---|---|---|---|---|---|---|---|---|---|---|
| | | VGI Ct Mean | non-VGI Ct Mean | Delta Ct | Type call via assay | VGII Ct Mean | non-VGII Ct Mean | Delta Ct | Type call via assay | VGIII Ct Mean | non-VGIII Ct Mean | Delta Ct | Type call via assay | VGIV Ct Mean | non-VGIV Ct Mean | Delta Ct | Type call via assay | |
| B7488 | VGI | 17.0 | 29.0 | 11.9 | VGI | 37.4 | 17.7 | −19.7 | non-VGII | 28.4 | 14.9 | −13.5 | non-VGIII | 32.4 | 16.3 | −16.1 | non-VGIV | VGI |
| B7496 | VGI | 18.2 | 28.0 | 9.8 | VGI | 35.3 | 19.0 | −16.3 | non-VGII | 24.5 | 16.4 | −8.1 | non-VGIII | 31.7 | 17.9 | −13.8 | non-VGIV | VGI |
| B8551 | VGI | 17.3 | 29.6 | 12.3 | VGI | 36.2 | 17.9 | −18.3 | non-VGII | 28.7 | 15.3 | −13.4 | non-VGIII | 39.0 | 16.7 | −22.3 | non-VGIV | VGI |
| B8852 | VGI | 21.1 | 30.9 | 9.8 | VGI | 36.5 | 21.9 | −14.6 | non-VGII | 27.8 | 19.1 | −8.8 | non-VGIII | 32.0 | 20.6 | −11.4 | non-VGIV | VGI |
| B8886 | VGI | 18.9 | 29.2 | 10.3 | VGI | 38.1 | 19.3 | −18.8 | non-VGII | 26.7 | 16.4 | −10.3 | non-VGIII | 32.3 | 17.9 | −14.4 | non-VGIV | VGI |
| B8887 | VGI | 15.9 | 28.3 | 12.4 | VGI | 23.6 | 15.5 | −8.1 | non-VGII | 33.6 | 16.2 | −17.4 | non-VGIII | 34.1 | 15.5 | −18.7 | non-VGIV | VGI |
| B8990 | VGI | 18.8 | 30.9 | 12.1 | VGI | 37.2 | 20.1 | −17.1 | non-VGII | 31.3 | 16.9 | −14.3 | non-VGIII | 40.0 | 19.3 | −20.7 | non-VGIV | VGI |
| B9009 | VGI | 21.6 | 31.0 | 9.4 | VGI | 36.5 | 23.1 | −13.4 | non-VGII | 28.6 | 19.4 | −9.2 | non-VGIII | 40.0 | 21.1 | −18.9 | non-VGIV | VGI |
| B4501 | VGI | 16.1 | 26.7 | 10.6 | VGI | 30.5 | 18.1 | −12.4 | non-VGII | 30.6 | 17.3 | −13.3 | non-VGIII | 29.4 | 16.4 | −13.0 | non-VGIV | VGI |
| B4503 | VGI | 15.9 | 27.2 | 11.2 | VGI | 32.7 | 18.6 | −14.1 | non-VGII | 33.8 | 17.9 | −15.9 | non-VGIII | 28.7 | 16.1 | −12.6 | non-VGIV | VGI |
| B4504 | VGI | 15.6 | 27.2 | 11.5 | VGI | 33.1 | 18.1 | −15.1 | non-VGII | 33.9 | 17.4 | −16.4 | non-VGIII | 28.7 | 15.8 | −13.0 | non-VGIV | VGI |
| B4516 | VGI | 15.3 | 26.8 | 11.5 | VGI | 31.5 | 17.6 | −13.9 | non-VGII | 33.4 | 16.8 | −16.6 | non-VGIII | 29.7 | 15.3 | −14.3 | non-VGIV | VGI |
| B5765 | VGI | 17.2 | 28.0 | 10.8 | VGI | 32.8 | 19.7 | −13.0 | non-VGII | 34.4 | 19.2 | −15.2 | non-VGIII | 29.0 | 16.3 | −12.7 | non-VGIV | VGI |
| B9018 | VGI | 17.7 | 30.0 | 12.3 | VGI | 34.6 | 17.9 | −16.7 | non-VGII | 31.8 | 18.6 | −13.2 | non-VGIII | 35.0 | 18.3 | −16.8 | non-VGIV | VGI |
| B9019 | VGI | 16.9 | 26.1 | 9.2 | VGI | 35.4 | 16.7 | −18.7 | non-VGII | 34.9 | 16.7 | −18.2 | non-VGIII | 30.5 | 16.8 | −13.7 | non-VGIV | VGI |
| B9021 | VGI | 21.4 | 32.9 | 11.5 | VGI | 33.4 | 19.9 | −13.5 | non-VGII | 32.7 | 20.5 | −12.2 | non-VGIII | 35.5 | 20.4 | −15.2 | non-VGIV | VGI |
| B9142 | VGI | 16.0 | 26.3 | 10.3 | VGI | 27.8 | 15.9 | −11.9 | non-VGII | 32.7 | 16.5 | −16.2 | non-VGIII | 31.7 | 16.6 | −15.1 | non-VGIV | VGI |
| B9149 | VGI | 17.7 | 26.8 | 9.1 | VGI | 28.5 | 17.5 | −11.0 | non-VGII | 28.5 | 18.2 | −10.3 | non-VGIII | 31.0 | 18.3 | −12.6 | non-VGIV | VGI |
| B6864 | VGIIa | 27.8 | 17.5 | −10.3 | non-VGI | 19.3 | 33.1 | 13.8 | VGII | 34.7 | 19.7 | −15.0 | non-VGIII | 40.0 | 16.1 | −23.9 | non-VGIV | VGII |
| B7395 | VGIIa | 28.9 | 18.8 | −10.1 | non-VGI | 21.3 | 32.6 | 11.3 | VGII | 40.0 | 19.2 | −19.2 | non-VGIII | 40.0 | 18.8 | −21.2 | non-VGIV | VGII |
| B7422 | VGIIa | 27.4 | 17.4 | −10.0 | non-VGI | 19.5 | 32.3 | 12.8 | VGII | 35.4 | 19.1 | −16.3 | non-VGIII | 40.0 | 15.6 | −24.4 | non-VGIV | VGII |
| B7436 | VGIIa | 27.8 | 17.9 | −9.9 | non-VGI | 20.7 | 35.4 | 14.7 | VGII | 36.5 | 16.9 | −19.6 | non-VGIII | 40.0 | 15.6 | −24.4 | non-VGIV | VGII |
| B7467 | VGIIa | 30.9 | 20.7 | −10.1 | non-VGI | 22.7 | 32.7 | 9.9 | VGII | 37.7 | 23.4 | −14.2 | non-VGIII | 40.0 | 19.1 | −20.9 | non-VGIV | VGII |
| CA-1014 | VGIIa | 27.9 | 17.7 | −10.2 | non-VGI | 19.7 | 32.1 | 12.4 | VGII | 34.6 | 20.8 | −13.8 | non-VGIII | 40.0 | 16.6 | −23.4 | non-VGIV | VGII |
| CBS-7750 | VGIIa | 31.1 | 20.9 | −10.2 | non-VGI | 21.8 | 34.1 | 12.3 | VGII | 33.1 | 23.4 | −9.8 | non-VGIII | 40.0 | 19.8 | −20.2 | non-VGIV | VGII |
| ICB-107 | VGIIa | 27.4 | 17.4 | −10.0 | non-VGI | 18.9 | 32.6 | 13.7 | VGII | 39.0 | 24.9 | −14.1 | non-VGIII | 40.0 | 16.3 | −23.7 | non-VGIV | VGII |
| NIH-444 | VGIIa | 28.9 | 18.7 | −10.1 | non-VGI | 22.9 | 35.1 | 12.2 | VGII | 36.0 | 22.7 | −13.3 | non-VGIII | 40.0 | 18.4 | −21.6 | non-VGIV | VGII |
| B8508 | VGIIa | 20.4 | 11.6 | −8.8 | non-VGI | 13.6 | 32.4 | 18.9 | VGII | 31.1 | 12.8 | −18.3 | non-VGIII | 40.0 | 11.0 | −29.0 | non-VGIV | VGII |
| B8512 | VGIIa | 27.2 | 17.3 | −9.9 | non-VGI | 18.8 | 33.1 | 14.3 | VGII | 38.0 | 25.5 | −12.5 | non-VGIII | 40.0 | 15.8 | −24.2 | non-VGIV | VGII |
| B8558 | VGIIa | 28.1 | 18.2 | −9.9 | non-VGI | 20.0 | 34.7 | 14.8 | VGII | 37.5 | 25.4 | −12.1 | non-VGIII | 40.0 | 15.6 | −24.4 | non-VGIV | VGII |
| B8561 | VGIIa | 24.9 | 14.9 | −10.0 | non-VGI | 17.0 | 33.2 | 16.2 | VGII | 34.9 | 17.7 | −17.2 | non-VGIII | 40.0 | 13.3 | −26.7 | non-VGIV | VGII |
| B8563 | VGIIa | 23.7 | 14.8 | −8.9 | non-VGI | 17.4 | 30.4 | 13.0 | VGII | 34.5 | 16.2 | −18.2 | non-VGIII | 29.1 | 14.9 | −14.2 | non-VGIV | VGII |
| B8567 | VGIIa | 23.5 | 14.6 | −8.9 | non-VGI | 16.7 | 30.6 | 13.9 | VGII | 31.4 | 15.7 | −15.6 | non-VGIII | 29.7 | 14.8 | −14.9 | non-VGIV | VGII |
| B8854 | VGIIa | 22.5 | 13.7 | −8.8 | non-VGI | 15.9 | 29.9 | 14.0 | VGII | 30.6 | 14.9 | −15.7 | non-VGIII | 30.1 | 14.3 | −15.9 | non-VGIV | VGII |
| B8889 | VGIIa | 26.5 | 17.7 | −8.8 | non-VGI | 20.3 | 34.2 | 14.0 | VGII | 34.1 | 19.1 | −15.0 | non-VGIII | 33.2 | 22.2 | −11.0 | non-VGIV | VGII |
| B9077 | VGIIa | 24.4 | 16.0 | −8.4 | non-VGI | 18.4 | 32.8 | 14.4 | VGII | 32.8 | 20.4 | −12.4 | non-VGIII | 32.2 | 17.3 | −14.9 | non-VGIV | VGII |
| B7394 | VGIIa | 25.6 | 17.0 | −8.6 | non-VGI | 19.4 | 34.1 | 14.7 | VGII | 33.8 | 18.2 | −15.6 | non-VGIII | 35.1 | 16.8 | −18.2 | non-VGIV | VGII |
| B7735 | VGIIa | 24.7 | 15.8 | −8.9 | non-VGI | 18.1 | 32.7 | 14.6 | VGII | 33.0 | 17.1 | −15.9 | non-VGIII | 33.2 | 15.8 | −17.4 | non-VGIV | VGII |
| B8555 | VGIIa | 28.0 | 17.6 | −10.4 | non-VGI | 20.3 | 33.1 | 12.7 | VGII | 34.5 | 16.2 | −18.2 | non-VGIII | 32.4 | 17.5 | −15.0 | non-VGIV | VGII |
| B8793 | VGIIa | 33.6 | 17.8 | −15.9 | non-VGI | 15.4 | 28.6 | 13.2 | VGII | 31.4 | 18.6 | −14.6 | non-VGIII | 40.0 | 18.6 | −21.4 | non-VGIV | VGII |
| B8849 | VGIIb | 27.3 | 19.8 | −7.5 | non-VGI | 18.6 | 34.0 | 15.4 | VGII | 40.0 | 18.6 | −21.5 | non-VGIII | 34.9 | 19.2 | −15.7 | non-VGIV | VGII |
| B9296 | VGIIb | 31.9 | 22.5 | −9.5 | non-VGI | 23.5 | 33.5 | 10.0 | VGII | 32.4 | 20.8 | −11.6 | non-VGIII | 40.0 | 20.2 | −19.8 | non-VGIV | VGII |
| B7394 | VGIIb | 26.9 | 17.8 | −9.1 | non-VGI | 18.3 | 33.3 | 15.0 | VGII | 33.7 | 19.3 | −14.4 | non-VGIII | 40.0 | 15.4 | −24.6 | non-VGIV | VGII |
| B7735 | VGIIb | 28.8 | 18.3 | −10.5 | non-VGI | 20.8 | 32.2 | 11.3 | VGII | 0.0 | 15.8 | 15.8 | VGIII | 40.0 | 18.3 | −21.7 | non-VGIV | VGIII |
| B8554 | VGIIb | | | | | | | | | 35.5 | 22.0 | −13.4 | non-VGIII | | | | | VGIII |

TABLE 4-continued

MLST SYBR MAMA Ct values and genotype assignments for VGI-VGIV

| Isolate ID | Strain type via MLST | VGI_MPD471 | | | VGII_MPD495 | | | | VGIII_MPD198 | | | | VGIV_MPD423 | | | | Final Call |
|---|---|---|---|---|---|---|---|---|---|---|---|---|---|---|---|---|---|
| | | VGI Ct Mean | non-VGI Ct Mean | Delta Ct | Type call via assay | VGII Ct Mean | non-VGII Ct Mean | Delta Ct | Type call via assay | VGIII Ct Mean | non-VGIII Ct Mean | Delta Ct | Type call via assay | VGIV Ct Mean | non-VGIV Ct Mean | Delta Ct | Type call via assay | |
| B8828 | VGIIb | 28.8 | 18.5 | -10.3 | non-VGI | 20.7 | 32.7 | 11.9 | VGII | 35.9 | 19.2 | -16.7 | non-VGIII | 40.0 | 31.9 | -8.1 | non-VGIV | VGII |
| B8211 | VGIIb | 22.9 | 12.8 | -10.1 | non-VGI | 15.1 | 30.1 | 15.1 | VGII | 33.0 | 13.9 | -19.0 | non-VGIII | 33.8 | 12.9 | -21.0 | non-VGIV | VGII |
| B8966 | VGIIb | 24.6 | 15.5 | -9.0 | non-VGI | 17.3 | 25.9 | 8.6 | VGII | 29.3 | 15.6 | -13.7 | non-VGIII | 28.9 | 14.7 | -14.2 | non-VGIV | VGII |
| B9076 | VGIIb | 40.0 | 17.5 | -22.5 | non-VGI | 17.1 | 27.5 | 10.5 | VGII | 40.0 | 18.4 | -21.6 | non-VGIII | 30.6 | 18.0 | -12.6 | non-VGIV | VGII |
| B9157 | VGIIb | 25.4 | 15.3 | -10.2 | non-VGI | 17.6 | 29.4 | 11.9 | VGII | 31.2 | 16.1 | -15.1 | non-VGIII | 31.6 | 16.1 | -15.5 | non-VGIV | VGII |
| B9170 | VGIIb | 26.2 | 16.9 | -9.3 | non-VGI | 17.5 | 28.7 | 11.2 | VGII | 29.5 | 17.6 | -11.9 | non-VGIII | 31.1 | 17.7 | -13.4 | non-VGIV | VGII |
| B9234 | VGIIb | 24.7 | 15.0 | -9.6 | non-VGI | 15.4 | 30.3 | 14.9 | VGII | 30.2 | 15.7 | -14.5 | non-VGIII | 33.3 | 15.8 | -17.5 | non-VGIV | VGII |
| B9290 | VGIIb | 24.8 | 16.0 | -8.8 | non-VGI | 15.9 | 34.1 | 18.2 | VGII | 30.6 | 20.8 | -9.7 | non-VGIII | 33.2 | 16.6 | -16.6 | non-VGIV | VGII |
| B9241 | VGIIb | 23.4 | 13.2 | -10.3 | non-VGI | 15.5 | 28.0 | 12.5 | VGII | 30.0 | 13.9 | -16.0 | non-VGIII | 34.0 | 13.5 | -20.5 | non-VGIV | VGII |
| B9428 | VGIIb | 25.2 | 14.4 | -10.7 | non-VGI | 18.7 | 28.3 | 9.6 | VGII | 30.2 | 15.5 | -14.7 | non-VGIII | 34.1 | 15.0 | -19.1 | non-VGIV | VGII |
| B6863 | VGIIb | 28.9 | 18.6 | -10.2 | non-VGI | 20.7 | 34.2 | 13.5 | VGII | 33.2 | 22.7 | -10.6 | non-VGIII | 40.0 | 18.1 | -21.9 | non-VGIV | VGII |
| B7390 | VGIIc | 27.7 | 18.3 | -9.5 | non-VGI | 19.9 | 33.9 | 13.9 | VGII | 39.5 | 24.7 | -14.8 | non-VGIII | 40.0 | 16.9 | -23.1 | non-VGIV | VGII |
| B7432 | VGIIc | 28.2 | 18.3 | -9.9 | non-VGI | 20.0 | 32.6 | 12.7 | VGII | 34.8 | 18.0 | -16.8 | non-VGIII | 40.0 | 17.2 | -22.8 | non-VGIV | VGII |
| B7434 | VGIIc | 25.6 | 16.2 | -9.4 | non-VGI | 17.7 | 34.5 | 16.8 | VGII | 34.4 | 17.9 | -16.5 | non-VGIII | 40.0 | 13.8 | -26.2 | non-VGIV | VGII |
| B7466 | VGIIc | 30.8 | 20.8 | -10.0 | non-VGI | 22.4 | 33.6 | 11.2 | VGII | 37.4 | 23.7 | -13.7 | non-VGIII | 40.0 | 19.5 | -20.5 | non-VGIV | VGII |
| B7491 | VGIIc | 26.9 | 17.3 | -9.6 | non-VGI | 19.2 | 33.0 | 13.8 | VGII | 0.0 | 16.8 | 16.8 | non-VGIII | 40.0 | 16.7 | -23.3 | non-VGIV | VGII |
| B7493 | VGIIc | 27.1 | 17.4 | -9.7 | non-VGI | 18.6 | 33.6 | 15.1 | VGII | 36.6 | 20.7 | -15.8 | non-VGIII | 40.0 | 16.1 | -23.9 | non-VGIV | VGII |
| B7641 | VGIIc | 26.0 | 17.3 | -8.7 | non-VGI | 18.7 | 32.3 | 13.7 | VGII | 34.3 | 20.0 | -14.3 | non-VGIII | 40.0 | 15.6 | -24.4 | non-VGIV | VGII |
| B7737 | VGIIc | 28.0 | 18.5 | -9.6 | non-VGI | 20.1 | 34.3 | 14.2 | VGII | 37.0 | 23.0 | -14.0 | non-VGIII | 40.0 | 18.0 | -22.0 | non-VGIV | VGII |
| B7765 | VGIIc | 22.5 | 13.0 | -9.5 | non-VGI | 14.5 | 34.1 | 19.6 | VGII | 33.1 | 23.4 | -9.7 | non-VGIII | 40.0 | 12.9 | -27.1 | non-VGIV | VGII |
| B8210 | VGIIc | 27.8 | 18.1 | -9.7 | non-VGI | 19.6 | 33.3 | 13.7 | VGII | 33.0 | 19.4 | -13.5 | non-VGIII | 40.0 | 16.8 | -23.2 | non-VGIV | VGII |
| B8214 | VGIIc | 27.1 | 17.7 | -9.5 | non-VGI | 19.8 | 34.9 | 15.1 | VGII | 34.1 | 20.1 | -14.0 | non-VGIII | 40.0 | 16.1 | -23.9 | non-VGIV | VGII |
| B8510 | VGIIc | 26.8 | 17.6 | -9.2 | non-VGI | 18.8 | 33.2 | 14.5 | VGII | 35.2 | 19.1 | -16.1 | non-VGIII | 40.0 | 15.6 | -24.4 | non-VGIV | VGII |
| B8549 | VGIIc | 26.8 | 16.2 | -10.6 | non-VGI | 18.7 | 33.5 | 14.8 | VGII | 37.4 | 20.5 | -16.9 | non-VGIII | 29.6 | 19.2 | -10.4 | non-VGIV | VGII |
| B8552 | VGIIc | 27.1 | 17.0 | -10.1 | non-VGI | 18.6 | 33.2 | 14.6 | VGII | 34.3 | 19.7 | -14.6 | non-VGIII | 40.0 | 16.6 | -23.4 | non-VGIV | VGII |
| B8571 | VGIIc | 28.8 | 19.4 | -9.4 | non-VGI | 21.5 | 33.4 | 11.9 | VGII | 34.5 | 22.8 | -11.8 | non-VGIII | 40.0 | 19.5 | -20.5 | non-VGIV | VGII |
| B8788 | VGIIc | 26.0 | 16.0 | -10.0 | non-VGI | 18.5 | 29.5 | 11.0 | VGII | 38.0 | 20.4 | -17.6 | non-VGIII | 40.0 | 16.6 | -23.4 | non-VGIV | VGII |
| B8798 | VGIIc | 36.0 | 24.7 | -11.4 | non-VGI | 26.5 | 33.3 | 6.8 | VGII | 37.2 | 19.2 | -18.0 | non-VGIII | 40.0 | 22.5 | -17.5 | non-VGIV | VGII |
| B8821 | VGIIc | 30.5 | 20.5 | -10.0 | non-VGI | 22.3 | 33.0 | 10.7 | VGII | 37.0 | 29.0 | -8.0 | non-VGIII | 40.0 | 18.7 | -21.3 | non-VGIV | VGII |
| B8825 | VGIIc | 27.4 | 17.8 | -9.6 | non-VGI | 19.6 | 33.7 | 14.1 | VGII | 36.0 | 20.5 | -15.5 | non-VGIII | 40.0 | 17.5 | -22.5 | non-VGIV | VGII |
| B8833 | VGIIc | 29.2 | 20.7 | -8.6 | non-VGI | 19.5 | 33.4 | 13.9 | VGII | 35.4 | 19.6 | -15.8 | non-VGIII | 40.0 | 15.5 | -24.5 | non-VGIV | VGII |
| B8838 | VGIIc | 29.2 | 19.1 | -10.1 | non-VGI | 21.5 | 32.8 | 11.3 | VGII | 32.9 | 22.3 | -10.6 | non-VGIII | 40.0 | 18.5 | -21.5 | non-VGIV | VGII |
| B8843 | VGIIc | 29.5 | 19.4 | -10.1 | non-VGI | 21.5 | 33.7 | 12.2 | VGII | 37.5 | 22.1 | -15.4 | non-VGIII | 40.0 | 19.1 | -20.9 | non-VGIV | VGII |
| B8853 | VGIIc | 33.3 | 23.1 | -10.2 | non-VGI | 24.8 | 33.7 | 8.9 | VGII | 34.2 | 27.8 | -6.4 | non-VGIII | 40.0 | 21.5 | -18.5 | non-VGIV | VGII |
| B9159 | VGIIc | 29.6 | 17.5 | -12.1 | non-VGI | 19.1 | 29.9 | 10.7 | VGII | 40.0 | 26.0 | -14.0 | non-VGIII | 40.0 | 18.0 | -22.0 | non-VGIV | VGII |
| B9227 | VGIIc | 24.4 | 15.3 | -9.1 | non-VGI | 15.5 | 28.1 | 12.6 | VGII | 27.9 | 19.2 | -8.7 | non-VGIII | 31.0 | 16.3 | -14.7 | non-VGIV | VGII |
| B9235 | VGIIc | 24.6 | 15.1 | -9.5 | non-VGI | 15.3 | 28.9 | 13.7 | VGII | 29.2 | 16.4 | -12.7 | non-VGIII | 31.2 | 15.9 | -15.3 | non-VGIV | VGII |
| B9244 | VGIIc | 27.3 | 18.4 | -8.9 | non-VGI | 18.5 | 31.8 | 13.3 | VGII | 28.2 | 21.0 | -7.2 | non-VGIII | 30.6 | 18.8 | -11.8 | non-VGIV | VGII |
| B9245 | VGIIc | 26.8 | 17.9 | -8.9 | non-VGI | 18.0 | 33.5 | 15.5 | VGII | 31.2 | 19.3 | -11.9 | non-VGIII | 34.2 | 18.5 | -15.6 | non-VGIV | VGII |
| B9295 | VGIIc | 28.6 | 19.5 | -9.1 | non-VGI | 19.9 | 40.0 | 20.1 | VGII | 33.6 | 25.5 | -8.1 | non-VGIII | 34.4 | 20.3 | -14.2 | non-VGIV | VGII |
| B9302 | VGIIc | 24.6 | 14.1 | -10.5 | non-VGI | 16.9 | 26.7 | 9.8 | VGII | 28.8 | 15.1 | -13.7 | non-VGIII | 31.5 | 14.1 | -17.3 | non-VGIV | VGII |
| B9374 | VGIIc | 24.8 | 14.2 | -10.6 | non-VGI | 18.2 | 27.3 | 9.1 | VGII | 29.1 | 15.2 | -13.9 | non-VGIII | 32.8 | 14.4 | -18.4 | non-VGIV | VGII |
| B7415 | VGIII | 26.8 | 15.9 | -10.9 | non-VGI | 35.0 | 17.7 | -17.3 | non-VGII | 12.4 | 27.1 | 14.7 | VGIII | 30.9 | 15.9 | -15.0 | non-VGIV | VGIII |
| B7495 | VGIII | 28.1 | 18.0 | -10.1 | non-VGI | 36.1 | 18.8 | -17.3 | non-VGII | 14.1 | 30.1 | 16.0 | VGIII | 31.8 | 17.6 | -14.2 | non-VGIV | VGIII |
| B8212 | VGIII | 26.0 | 15.7 | -10.3 | non-VGI | 35.3 | 17.0 | -18.3 | non-VGII | 12.4 | 28.5 | 16.1 | VGIII | 32.5 | 15.6 | -16.9 | non-VGIV | VGIII |
| B8260 | VGIII | 29.6 | 19.6 | -10.0 | non-VGI | 36.7 | 20.8 | -15.9 | non-VGII | 15.9 | 30.7 | 14.8 | VGIII | 36.0 | 19.1 | -16.9 | non-VGIV | VGIII |

TABLE 4-continued

MLST SYBR MAMA Ct values and genotype assignments for VGI-VGIV

| | | VGI_MPD471 | | | VGII_MPD495 | | | VGIII_MPD198 | | | VGIV_MPD423 | | | |
|---|---|---|---|---|---|---|---|---|---|---|---|---|---|---|
| Isolate ID | Strain type via MLST | VGI Ct Mean | non-VGI Ct Mean | Delta Ct | Type call via assay | VGII Ct Mean | non-VGII Ct Mean | Delta Ct | Type call via assay | VGIII Ct Mean | non-VGIII Ct Mean | Delta Ct | Type call via assay | VGIV Ct Mean | non-VGIV Ct Mean | Delta Ct | Type call via assay | Final Call |
| B8262 | VGIII | 27.2 | 17.2 | -10.0 | non-VGI | 33.8 | 18.3 | -15.5 | non-VGII | 13.5 | 30.0 | 16.4 | VGIII | 40.0 | 16.9 | -23.1 | non-VGIV | VGIII |
| B8516/B8616 | VGIII | 28.4 | 18.5 | -9.9 | non-VGI | 37.8 | 19.5 | -18.3 | non-VGII | 14.6 | 29.1 | 14.5 | VGIII | 31.8 | 18.0 | -13.8 | non-VGIV | VGIII |
| B9143 | VGIII | 28.6 | 18.3 | -10.3 | non-VGI | 38.3 | 19.6 | -18.7 | non-VGII | 14.5 | 30.2 | 15.7 | VGIII | 33.3 | 18.0 | -15.3 | non-VGIV | VGIII |
| B9146 | VGIII | 30.3 | 19.5 | -10.8 | non-VGI | 38.5 | 21.2 | -17.3 | non-VGII | 15.8 | 30.1 | 14.3 | VGIII | 31.2 | 19.3 | -11.9 | non-VGIV | VGIII |
| B8965 | VGIII | 26.2 | 16.8 | -9.4 | non-VGI | 30.6 | 17.1 | -13.5 | non-VGII | 16.1 | 30.6 | 14.5 | VGIII | 35.0 | 17.4 | -17.6 | non-VGIV | VGIII |
| B9148 | VGIII | 26.0 | 16.6 | -9.4 | non-VGI | 31.0 | 16.6 | -14.4 | non-VGII | 15.9 | 30.6 | 14.7 | VGIII | 32.8 | 17.4 | -15.4 | non-VGIV | VGIII |
| B9151 | VGIII | 25.7 | 16.5 | -9.3 | non-VGI | 30.7 | 16.2 | -14.4 | non-VGII | 15.4 | 30.3 | 14.9 | VGIII | 34.9 | 18.0 | -17.0 | non-VGIV | VGIII |
| B9163 | VGIII | 26.9 | 17.5 | -9.4 | non-VGI | 29.8 | 17.3 | -12.5 | non-VGII | 16.9 | 29.7 | 12.8 | VGIII | 33.4 | 18.0 | -15.4 | non-VGIV | VGIII |
| B9237 | VGIII | 26.7 | 17.9 | -8.9 | non-VGI | 31.6 | 17.4 | -14.2 | non-VGII | 17.3 | 35.0 | 17.7 | VGIII | 38.1 | 19.3 | -18.9 | non-VGIV | VGIII |
| B9372 | VGIII | 23.5 | 12.7 | -10.9 | non-VGI | 29.3 | 13.1 | -16.1 | non-VGII | 14.8 | 27.4 | 12.6 | VGIII | 32.6 | 13.0 | -19.6 | non-VGIV | VGIII |
| B9422 | VGIII | 23.9 | 12.8 | -11.1 | non-VGI | 28.9 | 12.9 | -15.9 | non-VGII | 14.6 | 26.8 | 12.2 | VGIII | 33.0 | 13.3 | -19.7 | non-VGIV | VGIII |
| B9430 | VGIII | 23.5 | 12.9 | -10.6 | non-VGI | 30.1 | 13.4 | -16.8 | non-VGII | 15.1 | 28.5 | 13.4 | VGIII | 35.5 | 13.4 | -22.0 | non-VGIV | VGIII |
| B7238 | VGIV | 25.2 | 16.4 | -8.8 | non-VGI | 33.2 | 18.5 | -14.7 | non-VGII | 34.6 | 17.9 | -16.7 | non-VGIII | 16.3 | 27.4 | 11.1 | VGIV | VGIV |
| B7240 | VGIV | 25.8 | 17.1 | -8.8 | non-VGI | 33.9 | 19.5 | -14.5 | non-VGII | 34.2 | 18.5 | -15.7 | non-VGIII | 17.0 | 28.8 | 11.8 | VGIV | VGIV |
| B7243 | VGIV | 26.1 | 17.3 | -8.8 | non-VGI | 32.0 | 19.6 | -12.4 | non-VGII | 32.3 | 18.7 | -13.6 | non-VGIII | 16.8 | 27.1 | 10.2 | VGIV | VGIV |
| B7247 | VGIV | 25.6 | 16.5 | -9.1 | non-VGI | 33.4 | 19.2 | -14.2 | non-VGII | 32.0 | 18.1 | -13.9 | non-VGIII | 16.3 | 28.4 | 12.1 | VGIV | VGIV |
| B7249 | VGIV | 23.4 | 14.8 | -8.6 | non-VGI | 31.6 | 16.7 | -14.9 | non-VGII | 32.6 | 16.0 | -16.6 | non-VGIII | 14.5 | 31.1 | 16.5 | VGIV | VGIV |
| B7260 | VGIV | 26.0 | 16.5 | -9.4 | non-VGI | 30.9 | 18.0 | -13.0 | non-VGII | 34.2 | 17.4 | -16.8 | non-VGIII | 15.7 | 27.0 | 11.2 | VGIV | VGIV |
| B7262 | VGIV | 26.3 | 16.8 | -9.5 | non-VGI | 31.4 | 18.7 | -12.7 | non-VGII | 33.4 | 18.0 | -15.4 | non-VGIII | 15.8 | 27.5 | 11.6 | VGIV | VGIV |
| B7263 | VGIV | 24.5 | 15.7 | -8.9 | non-VGI | 33.1 | 17.9 | -15.3 | non-VGII | 37.3 | 17.0 | -20.3 | non-VGIII | 15.8 | 28.0 | 12.2 | VGIV | VGIV |
| B7264 | VGIV | 24.4 | 15.0 | -9.4 | non-VGI | 31.2 | 16.9 | -14.3 | non-VGII | 30.6 | 16.0 | -14.6 | non-VGIII | 14.8 | 26.8 | 12.0 | VGIV | VGIV |
| B7265 | VGIV | 27.5 | 17.3 | -10.2 | non-VGI | 34.1 | 19.6 | -14.5 | non-VGII | 32.1 | 18.8 | -13.3 | non-VGIII | 16.9 | 28.8 | 11.9 | VGIV | VGIV |

TABLE 5

VGII subtyping SYBR MAMA Ct values and genotype assignments for VGIIa, b, c

| Isolate ID | Strain type via MLST | VGIIa_Assay_45211 | | | | VGIIb_Assay_502129 | | | | VGIIc_Assay_257655 | | | | Final Call |
|---|---|---|---|---|---|---|---|---|---|---|---|---|---|---|
| | | VGIIa Ct Mean | non-VGIIa Ct Mean | Delta Ct | Type call via assay | VGIIb Ct Mean | non-VGIIb Ct Mean | Delta Ct | Type call via assay | VGIIc Ct Mean | non-VGIIc Ct Mean | Delta Ct | Type call via assay | |
| B6864 | VGIIa | 17.2 | 30.5 | 13.3 | VGIIa | 31.0 | 17.5 | -13.5 | non-VGIIb | 40.0 | 27.8 | -12.2 | non-VGIIc | VGIIa |
| B7395 | VGIIa | 19.8 | 33.5 | 13.7 | VGIIa | 33.1 | 20.3 | -12.9 | non-VGIIb | 40.0 | 30.6 | -9.4 | non-VGIIc | VGIIa |
| B7422 | VGIIa | 18.3 | 33.6 | 15.4 | VGIIa | 26.4 | 17.6 | -8.8 | non-VGIIb | 39.2 | 28.6 | -10.6 | non-VGIIc | VGIIa |
| B7436 | VGIIa | 18.6 | 31.7 | 13.1 | VGIIa | 30.1 | 17.0 | -13.2 | non-VGIIb | 38.0 | 29.1 | -8.9 | non-VGIIc | VGIIa |
| B7467 | VGIIa | 20.5 | 37.3 | 16.8 | VGIIa | 35.1 | 20.3 | -14.7 | non-VGIIb | 40.0 | 30.9 | -9.1 | non-VGIIc | VGIIa |
| B8555 | VGIIa | 17.1 | 31.2 | 14.1 | VGIIa | 30.3 | 17.5 | -12.8 | non-VGIIb | 40.0 | 27.7 | -12.3 | non-VGIIc | VGIIa |
| B8577 | VGIIa | 20.8 | 36.8 | 16.0 | VGIIa | 32.8 | 20.8 | -12.1 | non-VGIIb | 40.0 | 31.4 | -8.6 | non-VGIIc | VGIIa |
| B8793 | VGIIa | 15.1 | 29.8 | 14.7 | VGIIa | 30.7 | 18.6 | -12.1 | non-VGIIb | 40.0 | 29.8 | -10.2 | non-VGIIc | VGIIa |
| B8849 | VGIIa | 19.8 | 34.4 | 14.6 | VGIIa | 33.6 | 20.2 | -13.4 | non-VGIIb | 40.0 | 30.6 | -9.4 | non-VGIIc | VGIIa |
| CA-1014 | VGIIa | 13.1 | 27.3 | 14.2 | VGIIa | 27.0 | 14.0 | -13.0 | non-VGIIb | 34.9 | 24.2 | -10.7 | non-VGIIc | VGIIa |
| CBS-7750 | VGIIa | 21.8 | 32.2 | 10.4 | VGIIa | 33.4 | 21.5 | -11.9 | non-VGIIb | 40.0 | 34.1 | -5.9 | non-VGIIc | VGIIa |
| ICB-107 | VGIIa | 21.8 | 33.6 | 11.8 | VGIIa | 33.2 | 21.2 | -12.0 | non-VGIIb | 40.0 | 33.8 | -6.2 | non-VGIIc | VGIIa |
| NIH-444 | VGIIa | 14.8 | 27.3 | 12.5 | VGIIa | 28.5 | 15.3 | -13.1 | non-VGIIb | 36.1 | 25.7 | -10.3 | non-VGIIc | VGIIa |
| B8508 | VGIIa | 17.0 | 27.8 | 10.8 | VGIIa | 26.5 | 17.3 | -9.2 | non-VGIIb | 31.7 | 22.7 | -9.1 | non-VGIIc | VGIIa |
| B8512 | VGIIa | 17.6 | 28.1 | 10.4 | VGIIa | 26.3 | 18.0 | -8.3 | non-VGIIb | 33.2 | 24.2 | -9.0 | non-VGIIc | VGIIa |
| B8558 | VGIIa | 16.3 | 24.8 | 8.5 | VGIIa | 27.3 | 15.3 | -12.0 | non-VGIIb | 29.4 | 20.0 | -9.4 | non-VGIIc | VGIIa |
| B8561 | VGIIa | 15.8 | 27.5 | 11.8 | VGIIa | 25.0 | 16.9 | -8.1 | non-VGIIb | 33.4 | 23.2 | -10.2 | non-VGIIc | VGIIa |
| B8563 | VGIIa | 14.5 | 27.3 | 12.8 | VGIIa | 23.9 | 15.6 | -8.3 | non-VGIIb | 31.7 | 21.7 | -10.0 | non-VGIIc | VGIIa |
| B8567 | VGIIa | 15.0 | 36.2 | 21.2 | VGIIa | 24.5 | 16.0 | -8.5 | non-VGIIb | 31.8 | 22.2 | -9.5 | non-VGIIc | VGIIa |
| B8854 | VGIIa | 14.7 | 26.7 | 12.0 | VGIIa | 24.1 | 15.1 | -9.0 | non-VGIIb | 31.4 | 22.2 | -9.2 | non-VGIIc | VGIIa |
| B8889 | VGIIa | 17.0 | 28.1 | 11.0 | VGIIa | 25.9 | 17.3 | -8.7 | non-VGIIb | 33.2 | 23.8 | -9.4 | non-VGIIc | VGIIa |
| B9077 | VGIIa | 16.7 | 27.8 | 11.1 | VGIIa | 25.6 | 16.7 | -9.0 | non-VGIIb | 32.9 | 24.4 | -8.4 | non-VGIIc | VGIIa |
| B9296 | VGIIa | 17.0 | 27.5 | 10.5 | VGIIa | 25.5 | 17.3 | -8.2 | non-VGIIb | 32.9 | 24.8 | -8.1 | non-VGIIc | VGIIa |
| B7394 | VGIIb | 40.0 | 19.0 | -21.0 | non-VGIIa | 17.3 | 29.6 | 12.3 | VGIIb | 40.0 | 29.0 | -11.0 | non-VGIIc | VGIIb |
| B7735 | VGIIb | 31.0 | 18.3 | -12.8 | non-VGIIa | 18.7 | 31.3 | 12.6 | VGIIb | 38.1 | 28.9 | -9.3 | non-VGIIc | VGIIb |
| B8554 | VGIIb | 32.9 | 21.2 | -11.7 | non-VGIIa | 22.2 | 35.0 | 12.8 | VGIIb | 40.0 | 30.4 | -9.6 | non-VGIIc | VGIIb |
| B8828 | VGIIb | 31.9 | 21.1 | -10.8 | non-VGIIa | 19.9 | 35.1 | 15.2 | VGIIb | 40.0 | 30.5 | -9.5 | non-VGIIc | VGIIb |
| B8211 | VGIIb | 27.8 | 16.9 | -10.9 | non-VGIIa | 17.4 | 28.8 | 11.4 | VGIIb | 32.3 | 22.3 | -10.0 | non-VGIIc | VGIIb |
| B8966 | VGIIb | 26.2 | 14.7 | -11.5 | non-VGIIa | 16.3 | 24.1 | 7.9 | VGIIb | 31.8 | 23.2 | -8.6 | non-VGIIc | VGIIb |
| B9076 | VGIIb | 30.0 | 18.8 | -11.2 | non-VGIIa | 19.7 | 30.9 | 11.4 | VGIIb | 39.1 | 27.0 | -12.1 | non-VGIIc | VGIIb |
| B9157 | VGIIb | 29.1 | 16.6 | -12.4 | non-VGIIa | 15.4 | 23.8 | 8.5 | VGIIb | 30.3 | 21.3 | -9.0 | non-VGIIc | VGIIb |
| B9170 | VGIIb | 26.6 | 15.4 | -11.2 | non-VGIIa | 16.9 | 24.8 | 7.9 | VGIIb | 31.0 | 22.7 | -8.3 | non-VGIIc | VGIIb |
| B9234 | VGIIb | 26.1 | 13.9 | -12.2 | non-VGIIa | 15.3 | 23.8 | 8.5 | VGIIb | 30.2 | 21.2 | -9.1 | non-VGIIc | VGIIb |
| B9290 | VGIIb | 26.1 | 13.8 | -12.3 | non-VGIIa | 15.1 | 24.5 | 9.5 | VGIIb | 30.6 | 21.2 | -9.5 | non-VGIIc | VGIIb |
| B9241 | VGIIb | 26.7 | 20.2 | -6.5 | non-VGIIa | 14.5 | 24.0 | 9.4 | VGIIb | 30.5 | 21.4 | -9.1 | non-VGIIc | VGIIb |
| B9428 | VGIIb | 27.5 | 14.8 | -12.6 | non-VGIIa | 16.0 | 24.3 | 8.2 | VGIIb | 32.0 | 22.4 | -9.6 | non-VGIIc | VGIIb |
| B6863 | VGIIc | 31.9 | 20.3 | -11.5 | non-VGIIa | 33.4 | 20.2 | -13.2 | non-VGIIb | 27.5 | 40.0 | 12.5 | VGIIc | VGIIc |
| B7390 | VGIIc | 32.7 | 18.9 | -13.8 | non-VGIIa | 31.1 | 17.9 | -13.2 | non-VGIIb | 25.9 | 40.0 | 14.1 | VGIIc | VGIIc |
| B7432 | VGIIc | 40.0 | 18.5 | -21.5 | non-VGIIa | 30.7 | 17.6 | -13.1 | non-VGIIb | 25.7 | 40.0 | 14.3 | VGIIc | VGIIc |
| B7434 | VGIIc | 27.5 | 15.5 | -12.0 | non-VGIIa | 28.5 | 15.4 | -13.1 | non-VGIIb | 23.3 | 40.0 | 16.7 | VGIIc | VGIIc |
| B7466 | VGIIc | 31.7 | 20.8 | -10.9 | non-VGIIa | 33.5 | 20.6 | -12.8 | non-VGIIb | 28.1 | 40.0 | 11.9 | VGIIc | VGIIc |
| B7491 | VGIIc | 28.7 | 17.4 | -11.2 | non-VGIIa | 30.4 | 16.9 | -13.5 | non-VGIIb | 24.0 | 40.0 | 16.0 | VGIIc | VGIIc |
| B7493 | VGIIc | 28.8 | 18.3 | -10.6 | non-VGIIa | 31.1 | 18.0 | -13.1 | non-VGIIb | 25.5 | 40.0 | 14.5 | VGIIc | VGIIc |
| B7641 | VGIIc | 29.2 | 17.2 | -12.0 | non-VGIIa | 30.0 | 17.2 | -12.8 | non-VGIIb | 24.5 | 40.0 | 15.5 | VGIIc | VGIIc |

TABLE 5-continued

VGII subtyping SYBR MAMA Ct values and genotype assignments for VGIIa, b, c

| Isolate ID | Strain type via MLST | VGIIa_Assay_45211 | | | VGIIb_Assay_502129 | | | VGIIc_Assay_257655 | | | Final Call |
|---|---|---|---|---|---|---|---|---|---|---|---|
| | | VGIIa Ct Mean | non-VGIIa Ct Mean | Delta Ct | Type call via assay | VGIIb Ct Mean | non-VGIIb Ct Mean | Delta Ct | Type call via assay | VGIIc Ct Mean | non-VGIIc Ct Mean | Delta Ct | Type call via assay | |
| B7737 | VGIIc | 32.6 | 20.1 | -12.5 | non-VGIIa | 30.8 | 20.5 | -10.4 | non-VGIIb | 28.4 | 40.0 | 11.6 | VGIIc | VGIIc |
| B7765 | VGIIc | 32.2 | 19.3 | -12.8 | non-VGIIa | 32.3 | 18.9 | -13.3 | non-VGIIb | 27.5 | 40.0 | 12.5 | VGIIc | VGIIc |
| B8210 | VGIIc | 29.7 | 17.6 | -12.0 | non-VGIIa | 30.1 | 17.4 | -12.7 | non-VGIIb | 25.9 | 40.0 | 14.1 | VGIIc | VGIIc |
| B8214 | VGIIc | 30.1 | 17.5 | -12.5 | non-VGIIa | 30.9 | 17.5 | -13.4 | non-VGIIb | 26.1 | 40.0 | 13.9 | VGIIc | VGIIc |
| B8510 | VGIIc | 29.6 | 17.5 | -12.0 | non-VGIIa | 31.0 | 17.3 | -13.7 | non-VGIIb | 24.5 | 40.0 | 15.5 | VGIIc | VGIIc |
| B8549 | VGIIc | 29.9 | 17.7 | -12.1 | non-VGIIa | 31.0 | 17.8 | -13.2 | non-VGIIb | 24.8 | 40.0 | 15.2 | VGIIc | VGIIc |
| B8552 | VGIIc | 29.2 | 17.1 | -12.0 | non-VGIIa | 30.3 | 17.2 | -13.1 | non-VGIIb | 24.4 | 40.0 | 15.6 | VGIIc | VGIIc |
| B8571 | VGIIc | 33.0 | 20.3 | -12.7 | non-VGIIa | 32.6 | 20.2 | -12.5 | non-VGIIb | 28.1 | 40.0 | 11.9 | VGIIc | VGIIc |
| B8788 | VGIIc | 29.1 | 17.3 | -11.7 | non-VGIIa | 30.0 | 17.2 | -12.8 | non-VGIIb | 25.0 | 40.0 | 15.0 | VGIIc | VGIIc |
| B8798 | VGIIc | 36.5 | 22.8 | -13.7 | non-VGIIa | 34.5 | 22.2 | -12.3 | non-VGIIb | 31.0 | 40.0 | 9.0 | VGIIc | VGIIc |
| B8821 | VGIIc | 37.7 | 24.5 | -13.2 | non-VGIIa | 37.1 | 24.4 | -12.7 | non-VGIIb | 33.0 | 40.0 | 7.0 | VGIIc | VGIIc |
| B8825 | VGIIc | 29.6 | 17.7 | -11.9 | non-VGIIa | 30.6 | 17.7 | -12.9 | non-VGIIb | 25.8 | 40.0 | 14.2 | VGIIc | VGIIc |
| B8833 | VGIIc | 29.0 | 17.0 | -12.0 | non-VGIIa | 30.1 | 17.0 | -13.1 | non-VGIIb | 25.2 | 40.0 | 14.8 | VGIIc | VGIIc |
| B8838 | VGIIc | 32.0 | 19.5 | -12.5 | non-VGIIa | 32.9 | 19.3 | -13.7 | non-VGIIb | 28.7 | 40.0 | 11.3 | VGIIc | VGIIc |
| B8843 | VGIIc | 32.4 | 19.9 | -12.5 | non-VGIIa | 33.0 | 19.5 | -13.5 | non-VGIIb | 28.6 | 40.0 | 11.4 | VGIIc | VGIIc |
| B8853 | VGIIc | 32.8 | 21.5 | -11.3 | non-VGIIa | 36.0 | 23.4 | -12.6 | non-VGIIb | 33.1 | 40.0 | 6.9 | VGIIc | VGIIc |
| B9159 | VGIIc | 27.4 | 20.3 | -7.1 | non-VGIIa | 25.8 | 16.7 | -9.1 | non-VGIIb | 20.5 | 34.5 | 14.0 | VGIIc | VGIIc |
| B9227 | VGIIc | 25.6 | 13.6 | -12.0 | non-VGIIa | 23.9 | 14.9 | -9.0 | non-VGIIb | 18.0 | 31.5 | 13.4 | VGIIc | VGIIc |
| B9235 | VGIIc | 25.9 | 13.7 | -12.1 | non-VGIIa | 24.1 | 14.9 | -9.2 | non-VGIIb | 18.4 | 32.4 | 14.0 | VGIIc | VGIIc |
| B9244 | VGIIc | 27.2 | 19.1 | -8.1 | non-VGIIa | 26.2 | 16.9 | -9.2 | non-VGIIb | 20.2 | 32.5 | 12.3 | VGIIc | VGIIc |
| B9245 | VGIIc | 28.4 | 22.9 | -5.5 | non-VGIIa | 25.2 | 17.4 | -7.8 | non-VGIIb | 20.7 | 34.5 | 13.8 | VGIIc | VGIIc |
| B9295 | VGIIc | 21.0 | 17.1 | -3.8 | non-VGIIa | 26.0 | 19.6 | -6.4 | non-VGIIb | 22.1 | 28.1 | 5.9 | VGIIc | VGIIc |
| B9302 | VGIIc | 26.7 | 15.6 | -11.1 | non-VGIIa | 23.7 | 15.4 | -8.3 | non-VGIIb | 19.4 | 34.3 | 15.0 | VGIIc | VGIIc |
| B9374 | VGIIc | 27.4 | 21.6 | -5.8 | non-VGIIa | 24.0 | 15.3 | -8.7 | non-VGIIb | 19.4 | 33.4 | 14.0 | VGIIc | VGIIc |

TABLE 6

Interassay and Intraassay for MLST and Subtyping MAMA

| Assay | interrun CV (%) | intrarun CV (%) |
|---|---|---|
| VGI | 4.33 | 1.36 |
| VGII | 2.35 | 0.22 |
| VGIII | 0.43 | 0.60 |
| VGIV | 1.37 | 1.08 |
| VGIIa | 0.22 | 0.50 |
| VGIIb | 1.27 | 0.92 |
| VGIIc | 1.61 | 0.32 |

TABLE 7

Lower limit dynamic range for MLST and subtyping MAMA primer sets

| Primer set tested | Limit (pg) | Median Ct |
|---|---|---|
| VGI | 0.5 | 31.7 |
| non-VGI | 0.5 | 31.1 |
| VGII | 0.5 | 29.5 |
| non-VGII | 0.5 | 28.7 |
| VGIII | 0.5 | 28.5 |
| non-VGIII | 0.5 | 29.9 |
| VGIV | 0.5 | 33.7 |
| non-VGIV | 0.5 | 33.2 |
| VGIIa | 0.5 | 30.2 |
| non-VGIIa | 0.5 | 31.2 |
| VGIIb | 0.5 | 30.1 |
| non-VGIIb | 0.5 | 28.5 |
| VGIIc | 0.5 | 37.4 |
| non-VGIIc | 0.05 | 39.4 |

---

What is claimed is:

1. A method of genotyping a *Cryptococcus gattii* sample, the method comprising the steps of:
    adding to a first mixture comprising the sample a first pair of primers where one primer comprises SEQ ID NO: 7 and the other primer comprises SEQ ID NO: 8;
    adding to a second mixture comprising the sample a second pair of primers where one primer comprises SEQ ID NO: 7 and the other primer comprises SEQ ID NO: 9;
    subjecting the first and second mixtures to conditions that allow nucleic acid amplification; and
    detecting a presence or an absence of a VGIIa genotype of the *Cryptococcus gattii* sample by detecting the nucleic acid amplifications of the first and second mixtures.

2. The method of claim 1 further comprising:

adding to a third mixture comprising the sample a third pair of primers where one primer comprises SEQ ID NO: 13 and the other primer comprises SEQ ID NO: 14;

adding to a fourth mixture comprising the sample a fourth pair of primers where one primer comprises SEQ ID NO: 13 and the other primer comprises SEQ ID NO: 15;

subjecting the third and fourth mixtures to conditions that allow nucleic acid amplification; and detecting a presence or an absence of a VGIIc genotype of the *Cryptococcus gattii* sample by detecting the nucleic acid amplifications of the third and fourth mixtures.

3. The method of claim 1, wherein detecting the nucleic acid amplifications comprises calculating a cycle threshold (Ct) value.

4. The method of claim 1, wherein the sample comprises an environmental sample.

5. The method of claim 1, wherein the sample is derived from a subject.

6. The method of claim 3, wherein amplification in the first and second mixtures indicates the presence of the VGIIa genotype of the *Cryptococcus gattii* sample when the absolute value of the difference between Ct values of the second mixture and the first mixture is less than 3.3.

7. The method of claim 2, wherein detecting the nucleic acid amplifications comprises calculating a cycle threshold (Ct) value, and wherein the amplification in the third and fourth mixtures indicates the presence of the VGIIc genotype of the *Cryptococcus gattii* sample when the absolute value of the difference between Ct values of the fourth mixture and the third mixture is less than 3.3.

8. The method of claim 1, further comprising:
adding to a third mixture comprising the sample a third pair of primers where one primer comprises SEQ ID NO: 10 and the other primer comprises SEQ ID NO: 11;
adding to a fourth mixture comprising the sample a fourth pair of primers where one primer comprises SEQ ID NO: 10 and the other primer comprises SEQ ID NO: 12;
subjecting the third and fourth mixtures to conditions that allow nucleic acid amplification; and
detecting a presence or an absence of a VGIIb genotype of the *Cryptococcus gattii* sample by detecting the nucleic acid amplifications of the third and fourth mixtures.

9. The method of claim 8, wherein detecting the nucleic acid amplifications comprises calculating a cycle threshold (Ct) value, and wherein the amplification in the third and fourth mixtures indicates the presence of the VGIIb genotype of the *Cryptococcus gattii* sample when the absolute value of the difference between Ct values of the fourth mixture and the third mixture is less than 3.3.

10. The method of claim 1, further comprising:
adding to a third mixture comprising the sample a third pair of primers where one primer comprises SEQ ID NO: 4 and the other primer comprises SEQ ID NO: 5;
adding to a fourth mixture comprising the sample a fourth pair of primers where one primer comprises SEQ ID NO: 4 and the other primer comprises SEQ ID NO: 6;
subjecting the third and fourth mixtures to conditions that allow nucleic acid amplification; and
detecting a presence or an absence of a VGII genotype of the *Cryptococcus gattii* sample by detecting the nucleic acid amplifications of the third and fourth mixtures.

11. The method of claim 10, wherein detecting the nucleic acid amplifications comprises calculating a cycle threshold (Ct) value, and wherein the amplification in the third and fourth mixtures indicates the presence of the VGII genotype of the *Cryptococcus gattii* sample when the absolute value of the difference between Ct values of the fourth mixture and the third mixture is less than 3.3.

12. The method of claim 1, further comprising:
adding to a third mixture comprising the sample a third pair of primers where one primer comprises SEQ ID NO: 1 and the other primer comprises SEQ ID NO: 2;
adding to a fourth mixture comprising the sample a fourth pair of primers where one primer comprises SEQ ID NO: 1 and the other primer comprises SEQ ID NO: 3;
subjecting the third and fourth mixtures to conditions that allow nucleic acid amplification; and
wherein the step of determining the detecting a presence or an absence of a VGI genotype of the *Cryptococcus gattii* sample by detecting the nucleic acid amplifications of the third and fourth mixtures.

13. The method of claim 12, wherein detecting the nucleic acid amplifications comprises calculating a cycle threshold (Ct) value, and wherein the amplification in the third and fourth mixtures indicates the presence of the VGI genotype of the *Cryptococcus gattii* sample when the absolute value of the difference between Ct values of the fourth mixture and the third mixture is less than 3.3.

14. The method of claim 1, further comprising:
adding to a third mixture comprising the sample a third pair of primers where one primer comprises SEQ ID NO: 16 and the other primer comprises SEQ ID NO: 17;
adding to a fourth mixture comprising the sample a fourth pair of primers where one primer comprises SEQ ID NO: 16 and the other primer comprises SEQ ID NO: 18;
subjecting the third and fourth mixtures to conditions that allow nucleic acid amplification; and
detecting a presence or an absence of a VGIII genotype of the *Cryptococcus gattii* sample by detecting the nucleic acid amplifications of the third and fourth mixtures.

15. The method of claim 14, wherein detecting the nucleic acid amplifications comprises calculating a cycle threshold (Ct) value, and wherein the amplification in the third and fourth mixtures indicates the presence of the VGIII genotype of the *Cryptococcus gattii* sample when the absolute value of the difference between Ct values of the fourth mixture and the third mixture is less than 3.3.

16. The method of claim 1, further comprising:
adding to a third mixture comprising the sample a third pair of primers where one primer comprises SEQ ID NO: 19 and the other primer comprises SEQ ID NO: 20;
adding to a fourth mixture comprising the sample a fourth pair of primers where one primer comprises SEQ ID NO: 19 and the other primer comprises SEQ ID NO: 21; and
subjecting the third and fourth mixtures to conditions that allow nucleic acid amplification,
detecting a presence or an absence of a VGIV genotype of the *Cryptococcus gattii* sample by detecting the nucleic acid amplifications of the third and fourth mixtures.

17. The method of claim 16, wherein detecting the nucleic acid amplifications comprises calculating a cycle threshold (Ct) value, and wherein the amplification in the third and fourth mixtures indicates the presence of the VGIV genotype of the *Cryptococcus gattii* sample when the absolute value of the difference between Ct values of the fourth mixture and the third mixture is less than 3.3.

* * * * *

UNITED STATES PATENT AND TRADEMARK OFFICE
CERTIFICATE OF CORRECTION

PATENT NO. : 9,994,917 B2
APPLICATION NO. : 14/819529
DATED : June 12, 2018
INVENTOR(S) : David Engelthaler et al.

Page 1 of 1

It is certified that error appears in the above-identified patent and that said Letters Patent is hereby corrected as shown below:

On the Title Page

Item (54): "CRYTOCOCCUS" should read --CRYPTOCOCCUS--

Item (71) Applicant: "THE TRANSLATION GENOMICS RESEARCH INSTITUTE" should read --THE TRANSLATIONAL GENOMICS RESEARCH INSTITUTE--

In the Specification

Column 1, Line 2: cancel the text "CRYTOCOCCUS", and insert the following text: --CRYPTOCOCCUS--

Column 1, Lines 7-8: "U.S. provisional application with application No. 62/033,769" should read --U.S. provisional application No. 62/033,769--

Column 4, Line 57: "5'3'" should read --5'→3'--

Column 6, Line 6: "ddTTP, and added to each of four reaction" should read --ddTTP), and added to each of four reactions--

Column 12, Line 41: "a Sheep, and a Cow" should read --a sheep, and a cow--

Signed and Sealed this
Sixth Day of November, 2018

Andrei Iancu
*Director of the United States Patent and Trademark Office*